United States Patent [19]

Chien et al.

[11] Patent Number: 5,145,682
[45] Date of Patent: Sep. 8, 1992

[54] TRANSDERMAL ABSORPTION DOSAGE UNIT FOR POSTMENOPAUSAL SYNDROME TREATMENT AND PROCESS FOR ADMINISTRATION

[75] Inventors: Yie W. Chien, North Brunswick; Te-Yen Chien, Branchburg, both of N.J.

[73] Assignee: Rutgers, The State University of New Jersey, New Brunswick, N.J.

[21] Appl. No.: 320,570

[22] Filed: Mar. 8, 1989

Related U.S. Application Data

[63] Continuation-in-part of Ser. No. 868,709, May 30, 1986, Pat. No. 4,883,669.

[51] Int. Cl.⁵ ............................................. A61F 13/02
[52] U.S. Cl. .................................. 424/448; 424/447; 424/449
[58] Field of Search ......................... 424/448, 449, 447

[56] References Cited

U.S. PATENT DOCUMENTS

| | | | |
|---|---|---|---|
| 3,896,934 | 12/1976 | Zaffaroni | 424/449 |
| 4,053,580 | 10/1977 | Chien et al. | 424/449 |
| 4,291,014 | 9/1981 | Keith et al. | 424/486 |
| 4,300,820 | 11/1981 | Shah | 424/80 X |
| 4,336,243 | 6/1982 | Sanvordeker et al. | 424/449 |
| 4,460,372 | 8/1984 | Campbell et al. | 424/486 |
| 4,693,887 | 8/1987 | Shah | 424/80 X |
| 4,906,169 | 3/1990 | Chien et al. | 424/448 |

Primary Examiner—Thurman K. Page
Assistant Examiner—Leon R. Horne
Attorney, Agent, or Firm—Leroy G. Sinn

[57] ABSTRACT

Transdermal absorption dosage units have been developed for treatment of postmenopausal syndrome which comprise a backing layer, an adjoining adhesive polymer layer in which at least minimum effective daily doses of an estrogen is microdispersed. Presently preferred is use of the natural estrogen, 17-beta-estradiol, or ethinyl estradiol or combinations thereof together with an amount of a natural progestogen or a progestin to minimize any potential side effects. The units use bioacceptable adhesive and polymers. An additional polymer layer in intimate contact with the estrogen-containing layer can be used. Also, a separating layer can optionally be used in making the dosage units, which separate the two adhesive polymer layers, which permits estrogen transmission from the first adhesive polymer layer during treatment. Dosage units are provided which transdermally deliver at least minimum daily doses of the estrogen for at least one day or for multiple days, such as for one week. The invention also provides a process for postmenopausal syndrome treatment using the novel dosage units.

20 Claims, 18 Drawing Sheets

TRANSDERMAL ABSORPTION DOSAGE UNIT FOR POSTMENOPAUSAL SYNDROME TREATMENT AND PROCESS FOR ADMINISTRATION

CROSS-REFERENCE TO RELATED APPLICATIONS

This application is a continuation-in-part of U.S. application Ser. No. 06/868,709, filed May 30, 1986 U.S. Pat. No. 4,883,669.

TECHNICAL FIELD

This invention relates to a novel transdermal absorption dosage unit adapted for postmenopausal syndrome treatment comprising a backing layer and an adjoining layer of a biologically acceptable adhesive polymer in which estradiol or another steroidal pharmaceutical having estrogenic activity is microdispersed in microreservoirs formed of selected transdermal absorption enhancing agents. The adhesive layer provides the means by which the dosage unit adheres to the skin of the subject being administered said estrogenic pharmaceutical and permits transdermal absorption of said estrogenic pharmaceutical. An amount of a progestin can also be incorporated into the adhesive polymer layer to diminish any side effects encountered in postmenopausal syndrome treatment. Additionally, the invention relates to an improved process for administration in postmenopausal syndrome treatment.

BACKGROUND ART

It has been found that certain pharmaceuticals are absorbed to a degree through the skin. This is referred to as transdermal pharmaceutical absorption. One means of effecting transdermal absorption has been to distribute the pharmaceutical within a polymeric disc or a container of a gel, which is brought into contact with an area of the skin of the subject to be treated with the pharmaceutical. Also, ointments or lotions containing a desired pharmaceutical have been applied to an area of the skin of the subject to be treated. Problems encountered in such treatment include inadequate control over the rate and duration of transdermal absorption or the rate can be too slow in the case of certain dosage forms, especially from pharmaceutical-containing discs or pharmaceutical-containing gel container dosage units or pads. It has been found that the transdermal absorption rates of certain pharmaceuticals can be increased by use of transdermal absorption enhancing agents with the pharmaceutical to be absorbed when compounding the polymeric disc or the pharmaceutical-containing gel.

It is desired to improve the dosage unit forms or devices by which pharmaceuticals are transdermally absorbed, especially in view of the importance of administration of pharmaceuticals by this means. Desired transdermal absorption of pharmaceuticals would provide an avoidance of gastrointestinal incompatibility with the pharmaceuticals and unwanted destruction of the pharmaceutical by metabolism in the gastrointestinal tract and by a "first pass" hepatic metabolism. The transdermal absorption minimizes inter- and intrapatient variations regarding such incompatibilities and metabolisms. By transdermal absorption, it is deemed possible to provide more constant pharmaceutical concentration in the body and to realize a greater pharmaceutical efficiency. It is possible, by proper transdermal absorption, to reduce the frequency of effective dosing. Transdermal administration provides most of the advantages of intravenous dosing without the necessity of hospitalization and the accompanying discomfort and inconvenience.

The estrogenic steroid estradiol is an illustration of a pharmaceutical in which great loss of orally administered estrogen occurs by first-pass through the liver, it being almost completely metabolized. Therefore, oral administration of estradiol is not a satisfactory means of replacing normal levels of estradiol. It has been found that by transdermal administration, estradiol can be provided, in only a fraction of the amount required in oral dosing, to achieve adequate levels of estradiol, which the body for one or more reasons is not naturally producing to provide adequate levels in women to prevent body conditions and symptoms caused by such inadequate levels. Also, by transdermal administration of estradiol, for example, the unwanted estradiol metabolites produced by first-pass hepatic metabolism are greatly reduced. An additional advantage of transdermal administration is the attainment of more constant levels of estradiol and other estrogenic steroids.

The need for estradiol replacement therapy is caused by menopause (the cessation of ovarian function), oophorectomy (loss of one or both ovaries by surgery) or by pituitary failure. Replacement estrogenic therapy is an important need. Besides the need to alleviate the menopausal symptoms caused by estrogenic steroid deficiency, there are additional contributions of such replacement estrogenic therapy associated with osteoporosis (loss of bone mass) and atherosclerosis. There is clearly a need for improvements in means and methods for postmenopausal syndrome and other estrogenic steroid therapy. Even though it has been found that estradiol itself or estradiol in the form of certain derivatives such as mono- or di-esters (e.g., acetate esters) can be absorbed transdermally, it is desired that improved transdermal estradiol and other estrogenic steroid absorption dosage unit forms and processes of transdermal administration be developed. A number of benefits would result.

SUMMARY OF INVENTION

This invention relates to a transdermal dosage unit for treatment of postmenopausal syndrome having the following:
a) a backing layer which is substantially impervious to an effective estrogen to be delivered transdermally from the adhesive polymer disc layer and any other components of the adhesive polymer disc layer; and
b) an adhesive layer which is adhered to said backing layer and which had dispersed therein microreservoirs an effective amount of an estrogen effective in treatment of postmenopausal syndrome, said adhesive polymers being biocompatible, compatible with said estrogen and permitting said estrogen to be transdermally absorbed; said adhesive polymer disc layer having one or more transdermal absorption enhancing agents microdispersed therein, said transdermal absorption agent or agents selected from biocompatible compounds having at least six carbon atoms and which are capable of forming microreservoirs during microdispersion with said adhesive polymer and estrogen to encapsulate said estrogen in said adhesive polymer used to make said adhesive polymer disc layer and being substantially insoluble or insoluble in water;

said dosage unit capable of delivering a dosage amount of said estrogen for at least seven successive days.

The microreservoirs suitably have diameters in the range of from about 1 to about 150 microns and desirably from about 2 to about 10 microns. It is understood that some minor amount by weight of the transdermal absorption enhancing agent component can be present in microreservoirs having diameters somewhat lesser or greater than the above referred to ranges so long as the effectiveness of the dosage units provided by this invention is retained.

The adhesive polymer layer also adheres the dosage unit in intimate contact with the skin of the subject being treated to permit the estrogen to be absorbed transdermally.

Optionally, an additional adhesive layer can be formed using the same or a different adhesive polymer which is also biocompatible and placed in intimate contact with the surface of the estrogen-containing adhesive polymer layer containing the estrogen steroid. This adhesive layer can contain one or more effective transdermal absorption enhancing agents or be free of these agents.

Optionally, another layer can be included in the dosage units between the estrogen-containing adhesive polymer layer and the adhesive layer which has present an effective amount of one or more enhancing agents. In this separating layer, it is preferable to have present little or no estrogen, progestin or enhancing agents. The separating layer can be made using adhesive polymers such as used in making the estrogen-containing adhesive polymer layer, for example, with a bioacceptable polyisobutylene or polyacrylic adhesive, which permits the estrogen in the layer to be transmitted for transdermal absorption being presently preferred. Additionally, it is presently preferred that the separating layer be free of any substantial amount of transdermal absorption enhancing agent.

The estrogen-containing adhesive polymer layer can alternatively be made with the estrogen such as estradiol present in microdispersed form without substantial use of the transdermal absorption enhancing agents described above.

The backing layer is made from materials that are substantially impermeable with regard to the pharmaceuticals of the transdermal dosage unit. It can be made of polymers such as polyethylene, polypropylene, polyvinylchloride, polyesters such as poly(ethylene phthalate), and foils such as laminates of polymer films with metallic foils such as aluminum foil.

The estrogen-containing adhesive layer is suitably fabricated from biologically acceptable adhesive polymers, such as a suitable polyacrylic adhesive polymers, silicone adhesive polymer or a polyisobutylene adhesive. The estrogen is suitably dispersed in the adhesive polymer. For example, it has been found suitable to form a mixture with a biocompatible, liquid transdermal absorption enhancing agent. It has been found in many cases that certain straight-chain saturated alkanols, such as n-decyl alcohol, work in a satisfactory manner in the mixture of estrogen and adhesive polymer. The adhesive polymer is added to the mixture of estrogen and n-decyl alcohol and the resulting combination is mixed and dispersed thoroughly. The estrogen-adhesive polymer mixture is applied as a thin layer to the backing layer and is dried. Care must be taken that the adhesive polymer selected is compatible with the estrogen and other active pharmaceuticals, permits their release for transdermal absorption and is free or sufficiently free from any biologically unacceptable components.

A suitable derivative of estradiol or other estrogenic steroids used in formulating the polymer matrix disc layer is commonly an ester which is biologically compatible and can be absorbed effectively transdermally. Also, it is ordinarily desired that such esters are bioconvertible by components of the skin or other portions of the body such as hydrolytical enzymes (e.g., esterase) to estradiol or other desired estrogenic steroid. If the derivative is an ester, the derivative can be a mono- or di-ester if the estrogenic steroid has two esterifiable groups. In the case of estradiol, it has hydroxy groups at the 3- and 17- positions and therefore the 3-mono and 17-mono as well as the 3,17 diesters can be made by generally known esterification methods. Some ester derivatives will be absorbed more readily than the basic estradiol or other estrogenic steroid. In selection of ester derivatives, it is ordinarily preferred that the ester derivative be absorbed more effectively than the basic compound and bioconverts efficiently, after absorption, to estradiol or other basic estrogenic steroid used. Valerate mono- and di-esters of estradiol are presently considered to be desirable esters. In formulating the adhesive layer, it is desirable at times to utilize two or more pharmaceuticals, such as the combination of a estradiol ester, like estradiol valerate, with an amount of estradiol. Also, one estrogenic steroid either in the form of the basic compound or derivative such as a bioconvertible ester, or combinations thereof, can be combined with another steroid which has a different efficacy, such as a progestogen or a synthetic progestin, in a suitable amount in order to minimize potential side effect of the estrogenic postmenopausal syndrome therapy.

It has been found suitable to add the natural progestogen, progesterone, or a synthetic progestin, such as levonorgestrel, in an appropriate amount to the estrogen-adhesive mixture used in making the adhesive layer.

It has further been found to be advantageous to add effective amounts of selected surfactants, such as biocompatible non-ionic surfactants sold under the designations Tween 20 and Tween 60, to the combination of estrogen such as estradiol and transdermal absorption enhancing agent, such as n-decyl alcohol. The amount of such surfactant used can vary. However, an amount of such surfactant in the range of 0.25 to 1 part based on 100 parts of the final estrogin-adhesive mixture used to form the adhesive layer has been found satisfactory.

The adhesive polymer layers can be formed by spraying or by solvent casting or laminating. The concentration of transdermal absorption enhancing agent, if employed, can be reduced in the portion of the adhesive polymer layer means, especially if less than desired adhesion is realized in the adhesive layer, by applying the surface portion of the adhesive layer separately wherein the adhesive composition has a lower concentration of transdermal absorption enhancing agent. The adhesive polymer layer is desirably thin in the micron-range thickness, suitably 10–200 microns in thickness, desirably about 20 to 180 microns, and preferably about 30 to 150 microns in thickness.

The absorption rate of the transdermal pharmaceutical absorption dosage units of the invention can be increased, such as by having an Enhancing Factor of at least 1.2, preferably at least 1.3, and more preferably at least about 1.5. Enhancing Factor is defined as the ratio of normalized permeation rate [in mcg/cm$^2$/hr] of a dosage unit of this invention with transdermal absorption enhancing agent/the normalized permeation rate of a corresponding dosage unit without enhancer.

The invention also is a process for administering said estrogen with or without added natural progestogen or synthetic progestin by applying said dosage unit to the skin of the subject to be treated, whereby said pharmaceuticals are transdermally administered to said subject to treat menopausal syndrome.

DETAILED DESCRIPTION OF THE INVENTION AND THE PREFERRED EMBODIMENTS

Figure 1:
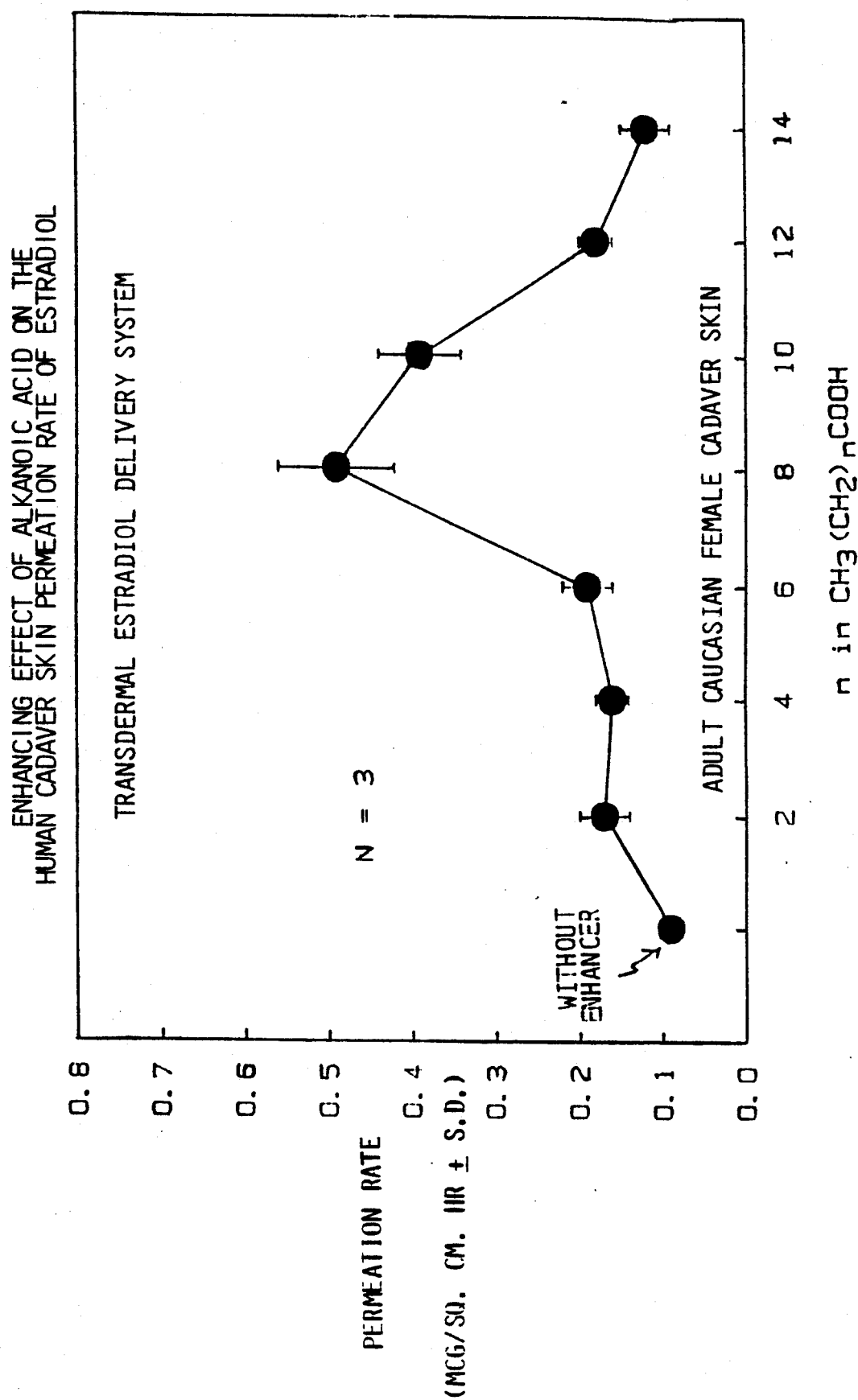
FIG. 1 is a graph showing the enhancing effect of alkanoic acid in a dosage unit on the human cadaver skin permeation rate of estradiol.
Figure 2:
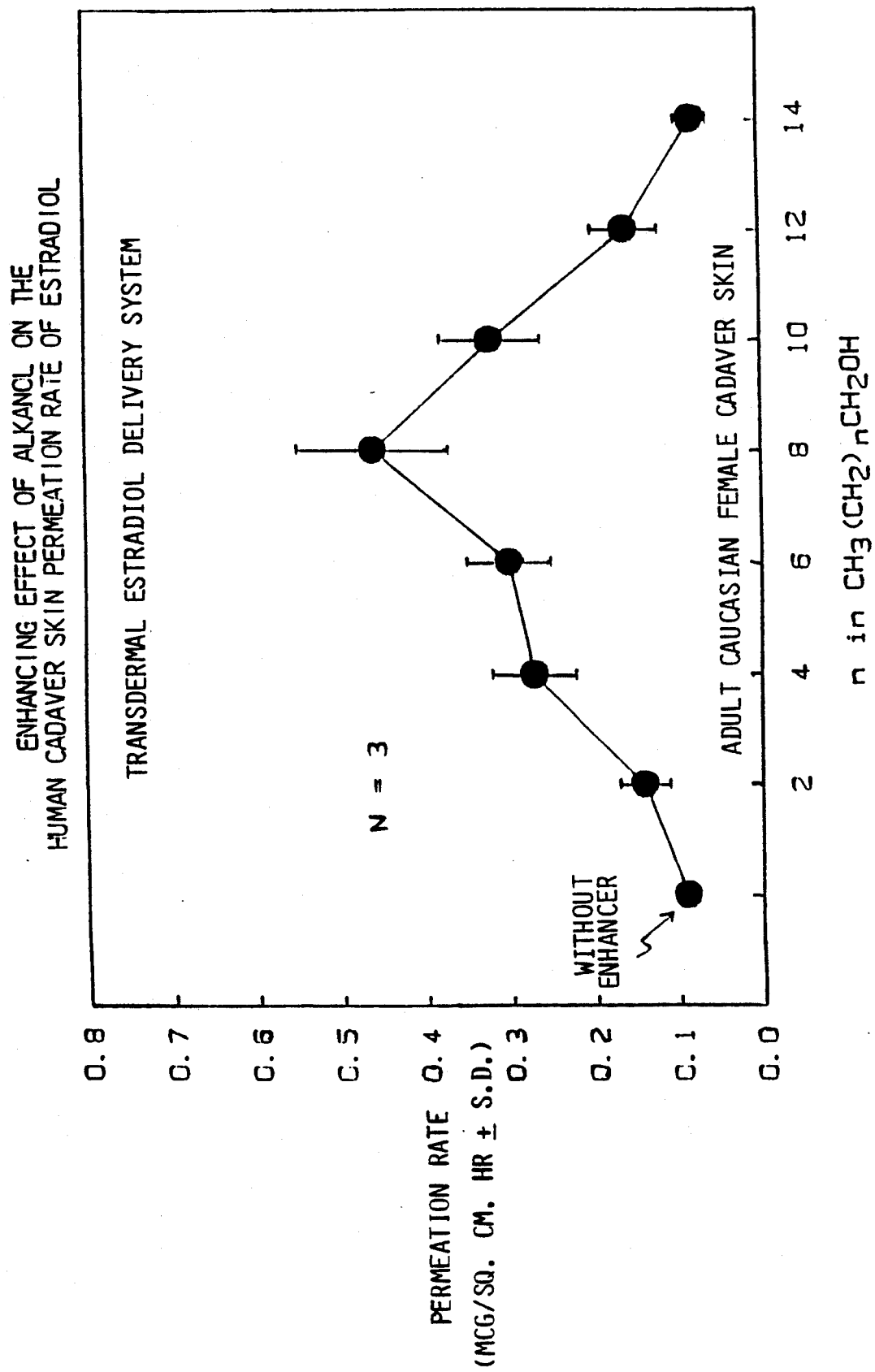
FIG. 2 is a graph showing the enhancing effect of alkanol in a dosage unit on the human cadaver skin permeation rate of estradiol as a function of alkyl chain length.
Figure 3:
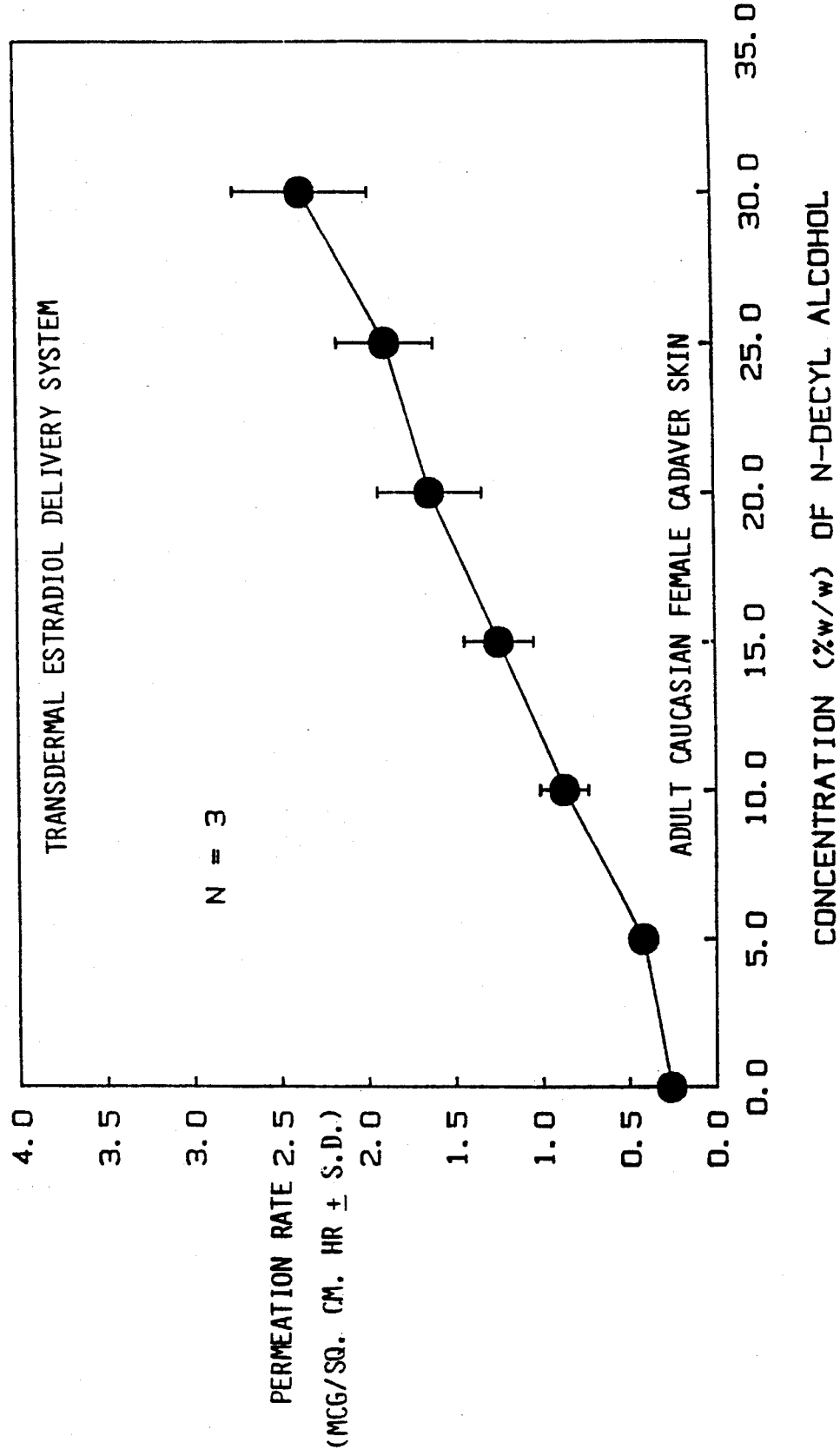
FIG. 3 is a graph showing the effect of concentration of n-decyl alcohol in a dosage unit on the human cadaver skin permeation rate of estradiol.
Figure 4:
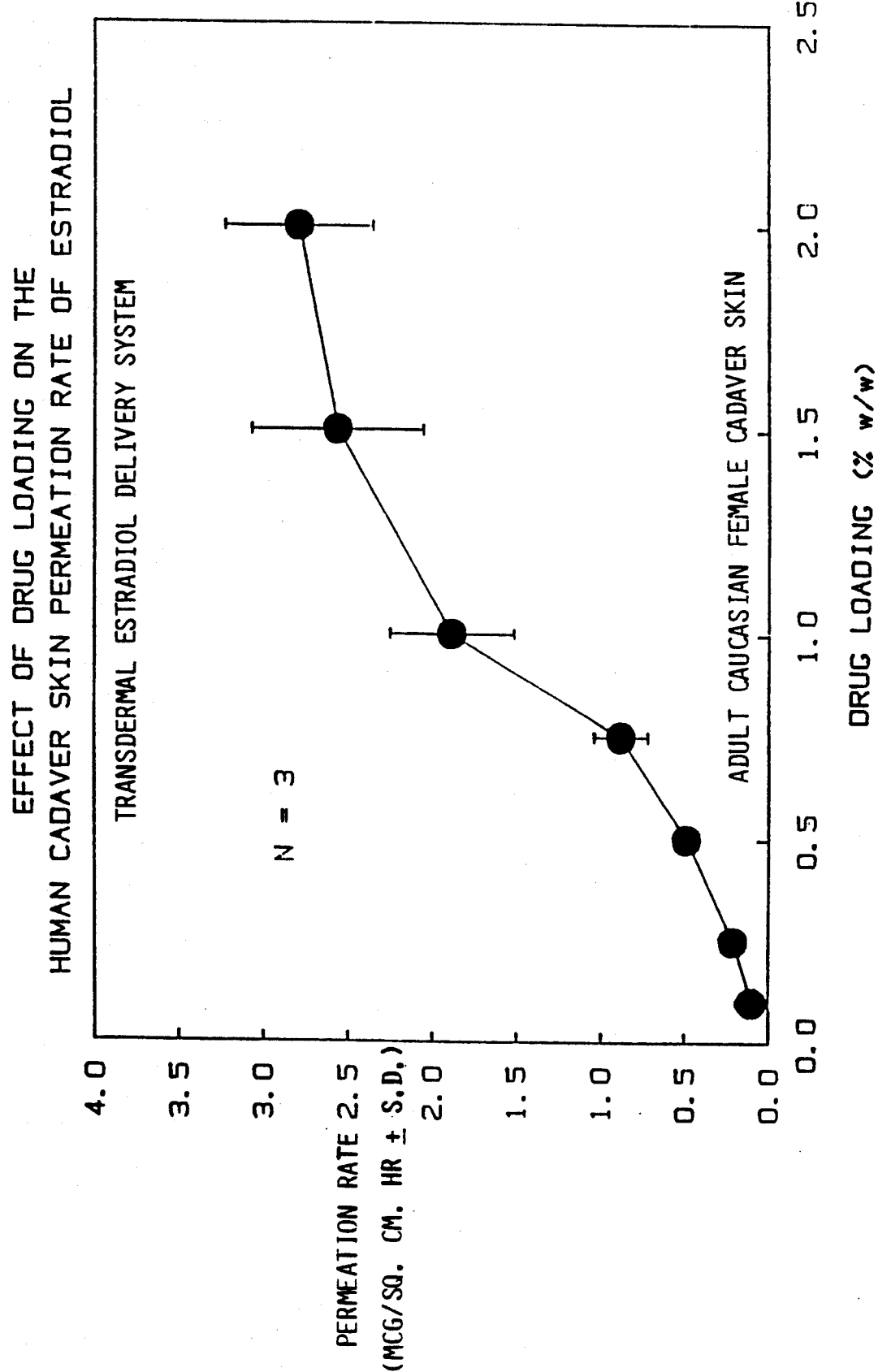
FIG. 4 is a graph showing the effect of drug loading in a dosage unit on the human cadaver skin permeation rate of estradiol.
Figure 5:
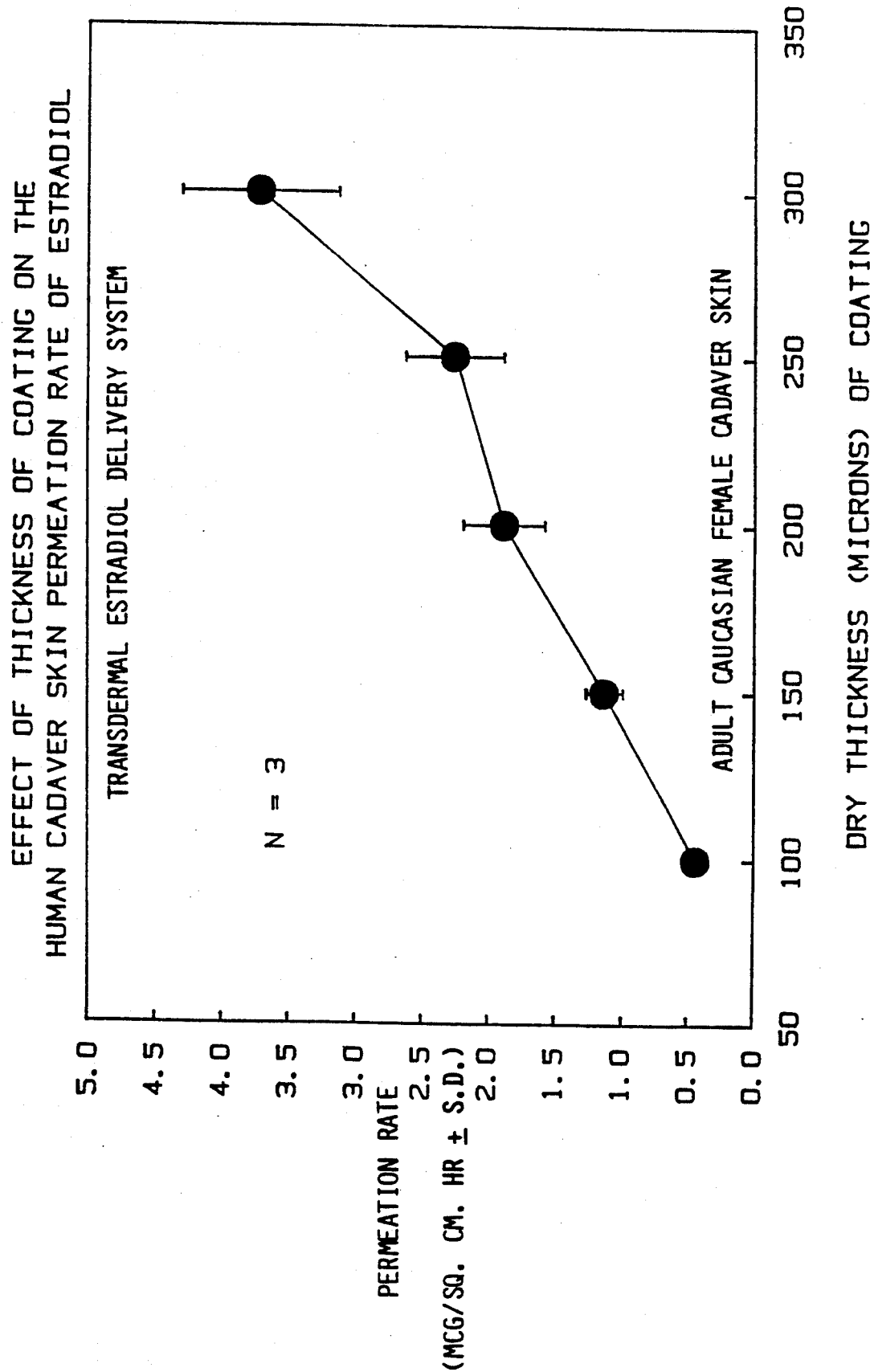
FIG. 5 is a graph showing the effect of thickness of coating in a dosage unit on the human cadaver skin permeation rate of estradiol.
Figure 6:
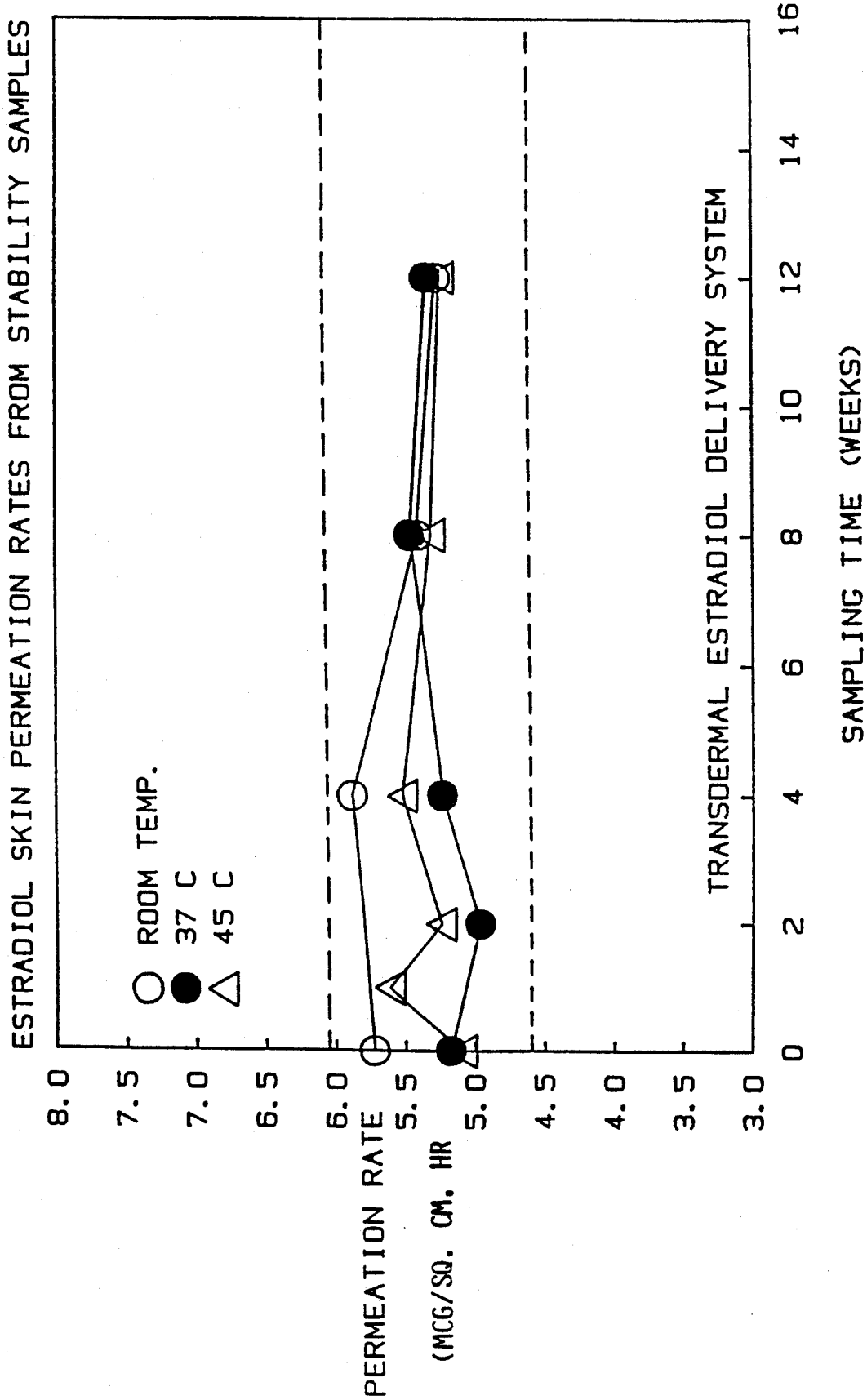
FIG. 6 is a graph showing estradiol skin permeation rates from dosage unit stability samples.

The backing layer can be made of any suitable material which is impermeable to the pharmaceuticals dispersed within the adjacent adhesive polymer layer. The backing layer serves as a protective cover for the estrogen-containing adhesive layer and provides also a support function. The backing can be formed so that it is essentially the same size layer as the estrogen-containing adhesive layer or it can be of larger dimension so that it can extend beyond the side of the estrogen-containing adhesive layer or overlay the side or sides of the estrogen-containing adhesive layer and then can extend outwardly in a manner that the surface of the extension of the backing layer can be a base for an adhesive to hold the dosage unit in intimate contact with the skin of the subject treated.

Examples of materials suitable for making the backing layer are films of high and low density polyethylene, polypropylene, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with polymer matrix layer. The backing layer can be any appropriate thickness which will provide the desired protective and support functions. A suitable thickness will be from about 10 to about 200 microns. Desirably, the thickness will be from about 15 to about 150 microns, and preferably be from about 20 to about 100 microns.

The adhesive layers are suitably made using a silicone based pressure sensitive adhesive, such as a (polydimethylsiloxane-silicate resin) copolymer adhesive depicted by the following formula:

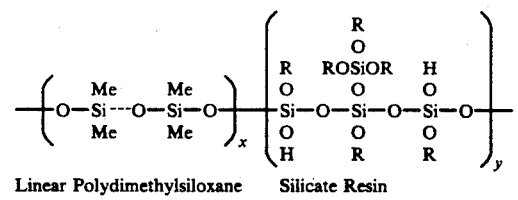

Linear Polydimethylsiloxane    Silicate Resin wherein Me is methyl and R is -Si(CH$_3$)$_3$ and x and y represent independent numbers of repeating units sufficient to provide the desired properties in the adhesive polymer and other polymer layers.

For example, adhesive polymer products or amine-resistant adhesive polymer products sold by Dow Corning, such as the ones sold under the designations of DC-355, Bio-PSA and X7-2920 medical adhesives, are suitable for use in making the adhesive layer. The adhesive polymer must be biologically acceptable and chemically compatible with the pharmaceuticals and the transdermal absorption enhancing agents. Certain polyacrylic adhesive polymers in the form of an alkyl ester, amide, free acid, or the like or polyisobutylene adhesive polymers can also be used with some pharmaceuticals utilized in the dosage units. Illustrative of suitable adhesive polymers for use in making the adhesive polymer layer are shown by the following formulas:

Polyisobutylene Adhesive

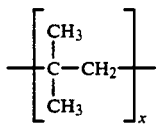

Polyacrylic Adhesive

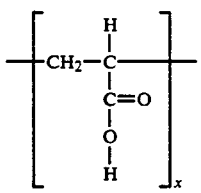

wherein x represents the number of repeating units sufficient to provide the desired properties in the adhesive polymer and R is H or lower alkyl including ethyl, butyl and 2-ethylhexyl.

Other suitable hypoallergenic pressure-sensitive contact adhesive compositions can also be used. A preferred adhesive layer is pressure sensitive.

The adhesive means then is finally covered in conventional therapeutic practice with a releasable protective film layer which is made from materials which are substantially impermeable to the pharmaceutical, the transdermal absorption enhancing agent and any other components of the dosage unit. The polymer materials and metal foil laminates used for the backing layer can be used to make the protective layer, provided the layer is made strippable or releasable such as by applying conventional siliconizing. A suitable releasable material for use with silicone polymer adhesive DC-355 and X7-2970 is Scotch Pak 1022 material sold by the 3M Company or Bio-Release material sold by Dow Corning.

In making the dosage units, the estrogen-containing adhesive layer can be made by dispersing an amount of estradiol crystals in an adhesive solution. For example, two parts of estradiol crystals can be added and dispersed in 98 parts of a biocompatible polyacrylate solution such as sold under the designation Duro-Tak 80-1054 by National Starch and Chemical Co. (has about 36% w/w of solid adhesive). An airtight container can be used for the mixing. The mixture can be made homogeneous by gently rotating the container.

The estradiol-containing mixture can then be readily coated onto a drug-impermeable backing layer such as a composite sold under the designation Scotch Pak 1109 by 3M Company. Coating equipment unit can be used to coat the backing layer to a desired thickness. A coater found satisfactory has been a Werner Mathis Laboratory Coater Type LTSV with built-in Laboratory drier LTF. The thickness of the estradiol-adhesive layer can be accurately controlled to a desired thickness, such as to 400 microns, using such a designed coater-drier.

If desired, an amount of a material progestogen can be added to the above mixture of estradiol and adhesive solution. The amount added will depend upon the amount desired in the estradiol-containing layer. The progestogen can be progesterone or other suitable compound within the class.

Instead of a natural progestogen, a synthetic progestin can be incorporated into the estradiol-adhesive solution prior to its use in coating.

The amount of the progestogen or progestin will depend on the estrogen used and the amount desired to diminish any toxic side effects. It has been found suitable, for example, to use about 1.0 to about 10 parts of progesterone per part of estradiol or about 0.5 to about 5 parts of a progestin such as levonorgestrel per part of estradiol used. If another estrogen is used, the amount of progestogen or progestin will be adjusted as necessary to provide a proper amount of the progestogen or progestin per part of estrogen.

Additionally, an effective amount of a transdermal absorption enhancing agent can be incorporated into the estradiol-adhesive solution used in the coating process. The enhancing agent suitably is biocompatible and chemically compatible with the drugs used. A suitable enhancing agent for this use has been found to be n-decyl alcohol, a liquid enhancing agent that is not removed in the normal coating and drying procedure for forming the estradiol-adhesive layer. If n-decyl alcohol is used as the enhancing agent, the amount can be varied depending upon the enhancement desired, the drugs used, and other factors. Ordinarily, a suitable amount can be selected from a range of about 1 part to 25 parts based on 100 parts of the adhesive polymer weight.

Other enhancing agents can be used instead of n-decyl alcohol. Other suitable agents have been found to be n-octanol, lauryl alcohol, caprylic acid, capric acid, and lauric acid. Other suitable agents will be suggested to those having skill in art in view of the disclosures hereof.

The estradiol-adhesive layer can be either covered with a suitable release liner (a poly(ethylene phthalate) laminated with aluminum foil) or a Teflon-coated polyester film such as sold under the designation Scotch-Pak 1022 (by 3M) or Bio-release X7-2741 or X7-2752 (by Dow Corning). The poly(ethylene phthalate) side to which the adhesive-enhancer-progestin coating is applied, is made strippable by conventional siliconizing or by other suitable means. The thickness of the adhesive-enhancer-progestin layer normally is suitably about 20 to about 1000 microns, preferably about 50 to about 500 microns.

Alternatively, the estradiol-adhesive layer can be covered with an adhesive layer which contains an amount of an enhancing agent. The additional adhesive layer is made as by dissolving the enhancing agent in the adhesive polymer solution or in a solvent which is compatible with the adhesive polymer solution used to make the adhesive layer containing the transdermal absorption enhancing agent. Any suitable amount of solvent can be used as necessary to dissolve the quantity of enhancer to be admixed with the adhesive polymer solution used. For example, 1 to 5 parts of solvent can be used to dissolve one part of transdermal absorption enhancing agent, depending upon the solubility of the enhancer. When using silicone-based adhesive solution, it has been found suitable to use 2 to 20 parts of transdermal absorption enhancing agent in 20 to 50 parts of solvent (such as acetone, methylene chloride, diethyl ether, methyl ethyl ketone, trifluorotrichloroethane or other suitable solvent) and add the solution to 100 parts of the adhesive solution. The enhancer-adhesive combination is thoroughly mixed and a coating thereof is applied using a film coating machine, such as referred to in the art as a coater equipped with K-bar or doctor blade, directly onto the estradiol-adhesive layer or to a strippable release liner and dried before laminating onto the polymer layer, as described above.

The amount of enhancer in the adhesive layer depends in part on the rapidity at which it is desired that the hormones be absorbed. Generally speaking, about 1 to about 40 percent of transdermal absorption permeation enhancer based on the weight of the adhesive is suitable, depending upon the enhancer, adhesive polymer, desired adhesiveness and other factors. Desirably, about 5 to about 30 percent of transdermal absorption enhancing agents are used depending upon the above recited factors. The adhesive layer containing the transdermal absorption enhancing agent is transferred to the estrogen-containing adhesive polymer layer surfaces by application of lamination technique under a constant pressure. In order to assure adequate adhesion of the adhesive polymer layer to the skin of the subject treated, additional adhesive polymer coating having a relatively low concentration of enhancer e.g., 1-20 percent based on the weight of the adhesive polymer can be further applied to the surface of enhancer-polymer layer. The thickness of this coating ordinarily is a minor percentage of the thickness of the final adhesive layer, such as 20-40 percent of the total adhesive polymer layer. The solvent of the respective coatings is removed by evaporation through a suitable drying process. The respective coatings can be combined to make the final multi-layer dosage form by application of lamination technique under a constant pressure or sequential solvent casting technique.

An optional separating layer can also be used and made of the adhesive materials. In making the separating layer, it has been found suitable to use a bioacceptable polyisobutylene having a suitable molecular weight. For example, the polyisobutylene used can suitably have a relative molecular mass Mv (viscosity average) of from about 400,000 to about 1,700,000, such as that of polyisobutylene sold by BASF under the designation Oppanol. One particular grade, B80, which has a relative molecular mass Mv (viscosity average) value of 850,000, is particularly suitable in making the separating layer. The viscosity average relative molecular mass is obtained from the equation: $J_o = 3.06 \times 10^{-2} \times Mv\ 0.65$. The viscosity or molecular weight should, generally speaking, be selected which is sufficiently high to provide a separating layer which is dimensionally stable and which is not excessively high so as to make fabrication of the separating layer unnecessarily difficult to provide a functional and pharmaceutically elegant dosage unit.

The thickness of the separating layer can vary as desired. However, it has been found that a coating layer with thickness (after removal of solvent) of about 30 to about 500 microns to be suitable, with a thickness of about 50 to 250 microns to be preferable. It has been found that a separating layer having about 100 micron thickness made of a polyisobutylene having a viscosity or molecular weight such as that of Oppanol B80 to function well, if the estrogen in the polymer layer is 17-beta-estradiol or ethinyl estradiol.

The separating layer should have sufficient thickness to minimize any migration, especially under prolonged storage conditions at elevated temperatures, such as 37° C. or 45° C. or greater. Also, the separating layer should be made of a suitable material and with a sufficient thickness to decelerate the rate of transmission of the estrogen in the adhesive polymer layer, as needed to provide a suitable delivery rate.

It has been found that the polymer solution of the separating layer can be made as by dissolving about 5 parts to about 20 parts, preferably at 10 parts of a suitable polyisobutylene, such as Oppanol B80 polyisobutylene in a suitable solvent, such as a mixture of cyclohexane, hexane and heptane (for example, a 1:1:1 mixture). The mixture is gently agitated such as by using a suitable rotator.

When the dissolution is substantially completed to provide a clear polyisobutylene solution, the solution can be used to coat onto a low adhesion film, such as a polyester film with a fluoropolymer-coated surface, for example, the material sold by 3M Company under the designation Scotch Pak 1022. A R.D. wireless coating bar (such as a #12) or laboratory coater Type LTSV by Werner Mathis can be used for coating. The resulting coating is dried and is repeated as necessary to obtain a layer of desired thickness, such as 100 microns. The separating layer thus formed can be assembled into the dosage unit by lamination to the polymer layer. Alternatively, the separating layer can be applied to the surface of the upper adhesive layer before being assembled by lamination to the surface of the lower adhesive polymer layer containing estrogen. The finished multi-layered adhesive polymer laminate can then be cut to form discs with desired shapes and sizes. The adhesive polymer layer discs generally should not exceed about 100 sq. cm in area, suitably about 5 to 100 sq. cm, preferably, about 8 to about 80 sq. cm, generally about 10 to 60 sq. cm being more preferable. The shape of the layer discs can vary; they can be circular, square, rectangular or other desired shape.

The dosage units are excised. The backing layer, if desired, can be shaped around the sides of the dosage unit, including the polymer layer, if such protection is desired. Also, a strippable layer can be placed over the face of the dosage unit for protection of the dosage unit. The resulting hormone adhesive polymer dosage unit forms are then placed in appropriate packaging for storage until they are to be applied in transdermal treatment.

The following examples are in illustration of the invention and are not intended to be limiting.

EXAMPLE 1

In a container, one (1) part of estradiol and 7.5 parts of progesterone were mixed with 25 parts of n-decyl alcohol to form a homogeneous dispersion. To this dispersion, 66.5 parts of polyacrylate adhesive polymer (Duro-Tak 80-1054 by National Starch and Chemical Co.) is added and the container is gently rotated to form a homogeneous mixture. This mixture is then coated onto a piece of Scotch Pak 1109 (3M Company) backing laminate by using a coating machine (Werner Mathis, Laboratory Coating Device, type LTSV). The thickness of coating is precisely set at 200 microns by the equipped micrometers on the coating machine. The coating is then dried at 50° C. for 45 minutes in the dryer (Werner Mathis, type LTF). The resulted coating is allowed to cool and then is laminated with the low-adhesion side of release liner (Scotch Pak 1022, 3M Co.) by using a laminating device equipped on the coating machine. The product thus obtained is cut into dosage units of suitable size by using a die cutter. The dosage units fabricated by this procedure were found to give in-vitro human cadaver skin permeation rates of estradiol and progesterone at 0.73±0.244 and 2.75±0.228 mcg/sq. cm/hr, respectively. By comparison, the in-vitro human cadaver skin permeation rate of estradiol delivered by the marketed Estraderm TTS-50 dosage unit was found to be 0.29±0.061 mcg/sq. cm/hr. Therefore, at the size of 10 sq. cm (the size of Estraderm TTS-50), the developed transdermal dosage unit will be able to deliver progesterone and estradiol combination at daily rates of 660±54.7 and 175.2±41.8 micrograms, respectively for one week while Estraderm TTS-50 dosage unit can only deliver estradiol alone at daily rate of 69.6±14.6 micrograms for 3-4 days.

The transdermal dosage units of this invention are evaluated by using a skin specimen from a "hairless" mouse or human cadaver by following the procedure described by Y. W. Chien, K. Valia and M. B. Doshi in *Drug Develop. & Ind. Pharm.*, 11(7) 1195-1212 (1985).

EXAMPLE 2

In a container, one (1) part of ethinyl estradiol and 0.5 parts of levonorgestrel are mixed with 25 parts of n-decyl alcohol to form a homogeneous dispersion. To this dispersion, 73.5 parts of polyacrylate adhesive polymer (Duro-Talk 80-1054, by National Starch and Chemical Co.) is added and the container is gently rotated to form a homogeneous mixture. This mixture is then coated onto a piece of Scotch Pak 1109 (3M Company) backing laminate by using a coating machine (Werner Mathis, Laboratory Coating Device, type LTSV). The thickness of coating is precisely set at 200 microns by the equipped micrometers on the coating machine. The coating is then dried at 50° C. for 45 minutes in the dryer (Werner Mathis, Laboratory Dryer, type LTF). The resulted coating is allowed to cool and then laminated with the low-adhesion side of release liner (Scotch Pak 1022, 3M Co.) by using a laminating device equipped on the coating machine. The product thus obtained is cut into dosage units of suitable size by using a die cutter. The dosage units fabricated by this procedure were found to give in-vitro human cadaver skin permeation rates of ethinyl estradiol and levonorgestrel at 0.64±0.124 and 0.15±0.034 mcg/sq. cm/hr, respectively. By comparison, the in-vitro human cadaver skin permeation rate of estradiol delivered by the marketed Estraderm TTS-50 dosage unit was found to be 0.29±0.061 mcg/sq. cm/hr. Therefore, at the size of 10 sq. cm (the size of Estraderm TTS-50), the developed transdermal dosage unit will be able to deliver levonorgestrel and ethynyl estradiol combination at daily rates of 36.0±8.16 and 153.6±29.76 micrograms, respectively, for one week while Estraderm TTS-50 dosage unit can only deliver estradiol alone at daily rate of 69.6±14.6 micrograms for 3-4 days.

The dosage units made according to the procedure of Example 2 have three layers in addition to the backing layer and the peelable release liner. At times herein are referred to as the following layers:

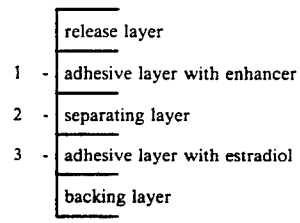

1 - Upper layer or adhesive layer with enhancer; 2 - Middle or separating layer; 3 - Lower or adhesive layer with estradiol.

The following are data on dosage units made following generally the procedure of Example 2:

TABLE 1

Effect of Thickness of Separating Layer on the Human Cadaver Skin Permeation Rate of Estradiol

| Thickness (microns) | Human Cadaver Skin Permeation Rate of Estradiol (mcg/sq. cm/hr ± S.D. N = 3) Type of Estradiol Reservoir Polymer | |
|---|---|---|
| | Silicone | Polyacrylate |
| 0 | 0.29 (0.060) | 1.08 (0.301) |
| 50 | 0.17 (0.032) | 0.51 (0.057) |
| 100 | 0.15 (0.027) | 0.34 (0.026) |
| 200 | 0.14 (0.021) | 0.30 (0.022) |
| 300 | 0.14 (0.007) | 0.27 (0.093) |
| 400 | 0.10 (0.015) | 0.23 (0.013) |
| 500 | 0.09 (0.013) | 1.08 (0.301) |
| Estraderm TTS-50 | 0.45 (0.021) | |

Notes:
1. Adult (65 year old) caucasian male cadaver skin was used.
2. Duration of experiment is 140 hours with 10 samples taken.
3. Separating layer made of Oppanol B80.

TABLE 2

Effect of Chain Length of Fatty Alcohols on the Human Cadaver Skin Permeation Rate of Estradiol

| n in $CH_3(CH_2)_nCH_2OH$ | Estradiol Skin Permeation Rate mcg/sq. cm/hr ± S.D. N = 3) |
|---|---|
| 2 | 0.19 (0.031) |
| 4 | 0.21 (0.022) |
| 6 | 0.46 (0.059) |
| 8 | 0.51 (0.057) |
| 10 | 0.29 (0.049) |
| 12 | 0.17 (0.024) |
| Estraderm TTS-50 | 0.41 (0.044) |

Notes:
1. Adult (65 year old) caucasian male cadaver skin was used.
2. Duration of experiment is 122 hours with 10 samples taken.

TABLE 3

Effect of Estradiol Loading Dose in the Reservoir Polymer on the Human Cadaver Skin Permeation Rate of Estradiol

| Loading Dose (% W/W) of Estradiol | Human Cadaver Skin Permeation Rate mcg/sq. cm/hr ± S.D. N = 3) |
|---|---|
| 0.10 | 0.04 (0.009) |
| 0.25 | 0.09 (0.011) |
| 0.50 | 0.16 (0.027) |
| 1.00 | 0.21 (0.024) |
| 1.50 | 0.42 (0.049) |
| 2.00 | 0.51 (0.057) |
| 2.50 | 0.50 (0.074) |
| Estraderm TTS-50 | 0.42 (0.046) |

Notes:
1. Adult (65 year old) caucasian male cadaver skin was used.
2. Duration of experiment is 120 hours with 10 samples taken.

TABLE 4

Effect of Thickness of Enhancer-containing Upper Adhesive Layer on the Human Cadaver Skin Permeation Rate of Estradiol

| Thickness (microns) of Upper Layer | Human Cadaver Skin Permeation Rate mcg/sq. cm/hr ± S.D. N = 3) |
|---|---|
| 100 | 0.21 (0.043) |
| 200 | 0.40 (0.081) |
| 300 | 0.52 (0.123) |
| 400 | 0.51 (0.057) |
| 500 | 0.42 (0.049) |
| 600 | 0.31 (0.062) |
| 700 | 0.26 (0.044) |
| Estraderm TTS-50 | 0.45 (0.021) |

Notes:
1. Adult (65 year old) caucasian male cadaver skin was used.
2. Duration of experiment is 96 hours with 10 samples taken.

TABLE 5

Effect of Concentration of n-Decyl Alcohol in the Upper Adhesive Layer on the Human Cadaver Skin Permeation Rate of Estradiol

| Concentration (% W/W) of n-Decyl Alcohol | Human Cadaver Skin Permeation Rate mcg/sq. cm/hr ± S.D. N = 3) |
|---|---|
| 0 | 0.03 (0.006) |
| 10 | 0.10 (0.011) |
| 15 | 0.25 (0.071) |
| 20 | 0.52 (0.074) |
| 25 | 0.69 (0.089) |
| 30 | 0.89 (0.214) |
| Estraderm TTS-50 | 0.45 (0.021) |

Notes:
1. Adult (65 year old) caucasian male cadaver skin was used.
2. Duration of experiment is 96 hours with 10 samples taken.

EXAMPLE 3

Two (2) parts of estradiol crystals are dispersed in 98 parts of polyacrylate adhesive solution (Duro-Tak 80-1054, National Starch and Chemical Co., containing 36% W/W of solid) in an air tight container. The container is rotated at 10 rpm under ambient temperature for 10 minutes to allow gentle mixing of estradiol with the adhesive solution. A homogeneous estradiol/adhesive dispersion can be obtained in this step. This estradiol/adhesive dispersion is then coated onto a drug-impermeable backing composite (Scotch Pak 1109, 3M Co.) which is mounted on the coating frame of a laboratory coater/dryer unit (Werner Mathis Laboratory Coater Type LTSV with Laboratory Dryer LTF). The thickness of this coating is precisely controlled at 400 microns by the micrometers equipped on the coating station of this coater/dryer unit. The coating is dried at 50° C. for 10 minutes in the dryer which is equipped with a sophisticated temperature and time controller. The intermediate product (1) thus formed is the estradiol-loaded reservoir lower layer as shown in FIG. 1.

Ten (10) parts of polyisobutylene polymer (Oppanol B80, BASF Co.) is dissolved in 90 parts of a solvent system to form a clear polymer solution. The solvent system contains mixture of cyclohexane, n-hexane and n-heptane at 1:1:1 ratio. This polyisobutylene polymer solution is then coated onto the low-adhesion side of a release liner (Scotch Pak 1022, 3M Co.) which is mounted on the coating frame of the same laboratory coater/dryer unit described in the first paragraph. The thickness of coating is 50 microns which is also precisely controlled by the micrometers equipped on the coating station of the coater/dryer unit. This coating is dried at 50° C. for 5 minutes in the LTF Dryer to form the intermediate product (2) which contains the permeability-regulating partition separating layer of the system, as shown in the diagram of Example 2.

The intermediate product (2) is then removed from the coating frame and laminated onto the estradiol-loaded reservoir layer of intermediate product (1) by using a laminating device equipped on the coating station of LTSV coater. After the lamination, the peelable release liner of intermediate product (2) is peeled off which allows the polyisobutylene polymer coating of intermediate product (2) to be transferred to the estradiol-loaded reservoir layer of intermediate product (1). The combined structure is hereafter called the intermediate product (3).

Twenty (20) parts of n-decyl alcohol is mixed with 80 parts of polyacrylate adhesive solution (Duro Tak 80-1054, National Starch and Chemical Co., containing 36% W/W of solid) in an air-tight container. The container is rotated gently at 10 rpm on a rotator for 10 minutes at ambient temperature until a homogeneous solution is obtained. A 400 microns thick of this solution is then coated onto the polyisobutylene coating layer of intermediate product (3) using the same LTSV Coater described in the previous paragraphs. The coating is dried in the LTF Oven at 50° C. for 30 minutes to form the intermediate product (4).

To complete the fabrication of this tri-layer transdermal estradiol delivery system, a piece of release liner (Scotch Pak 1022, 3M Co.) is laminated, using the laminating device of the LTSV Coater, onto the intermediate product (4) with the low-adhesion releasing surface facing the coated surface of intermediate product (4). The product thus formed is thereafter called intermediate product (5).

The intermediate product 95) can be cut into transdermal dosage units of specific size and shape by using a stainless steel die cutter. The final product of this fabrication process, Rutgers' tri-layer transdermal estradiol delivery system, has the multilayer structure as shown in FIG. 1.

Figure 7:
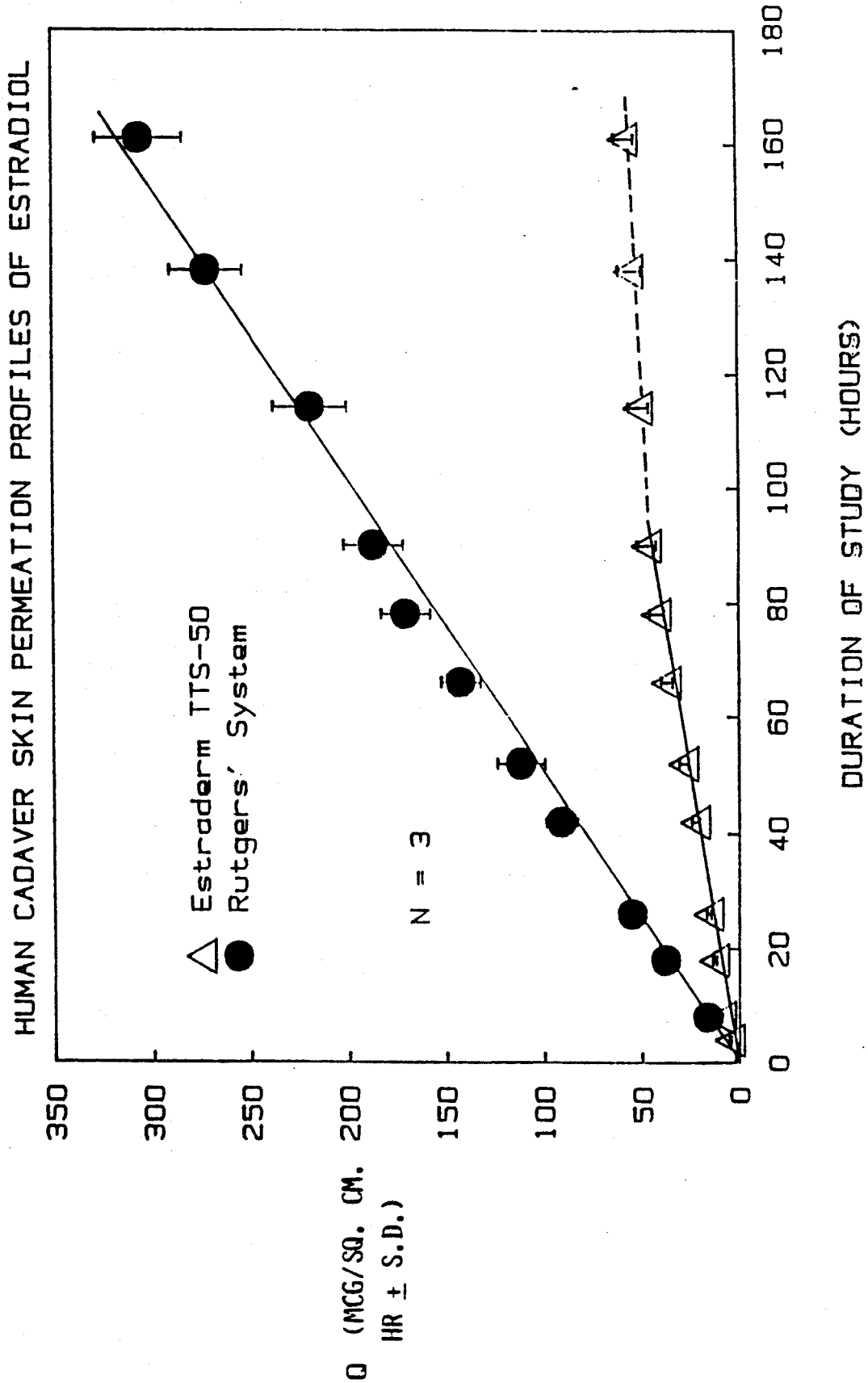
FIG. 7 is a graph comparing human cadaver skin permeation profiles of estradiol absorbed from the Rutgers dosage units as compared to Estraderm TTS-50.
Figure 8:
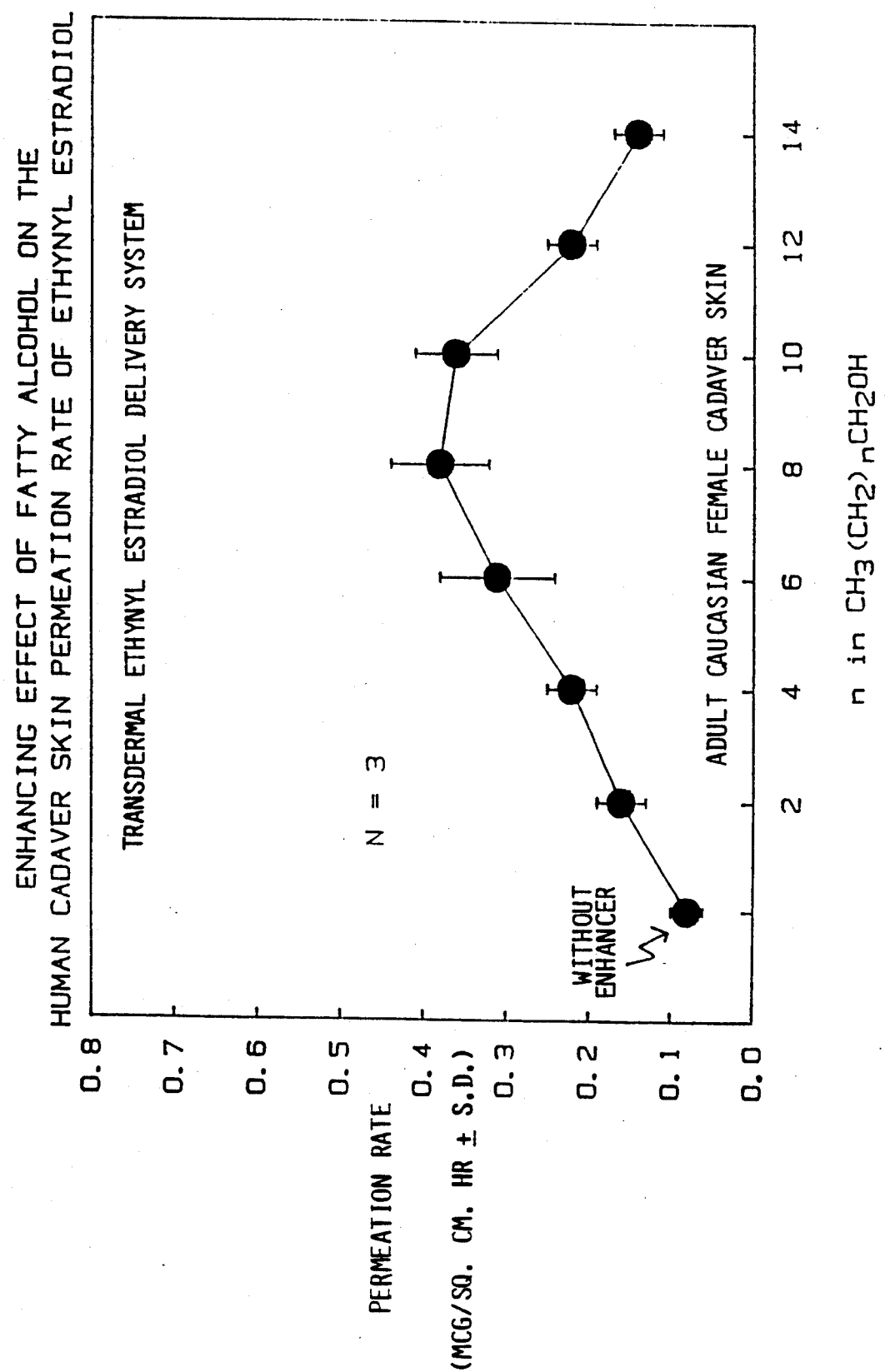
FIG. 8 is a graph showing the enhancing effect of alkanols in a dosage unit on the human cadaver skin permeation rate of ethinyl estradiol as a function of alkyl chain length.
Figure 9:
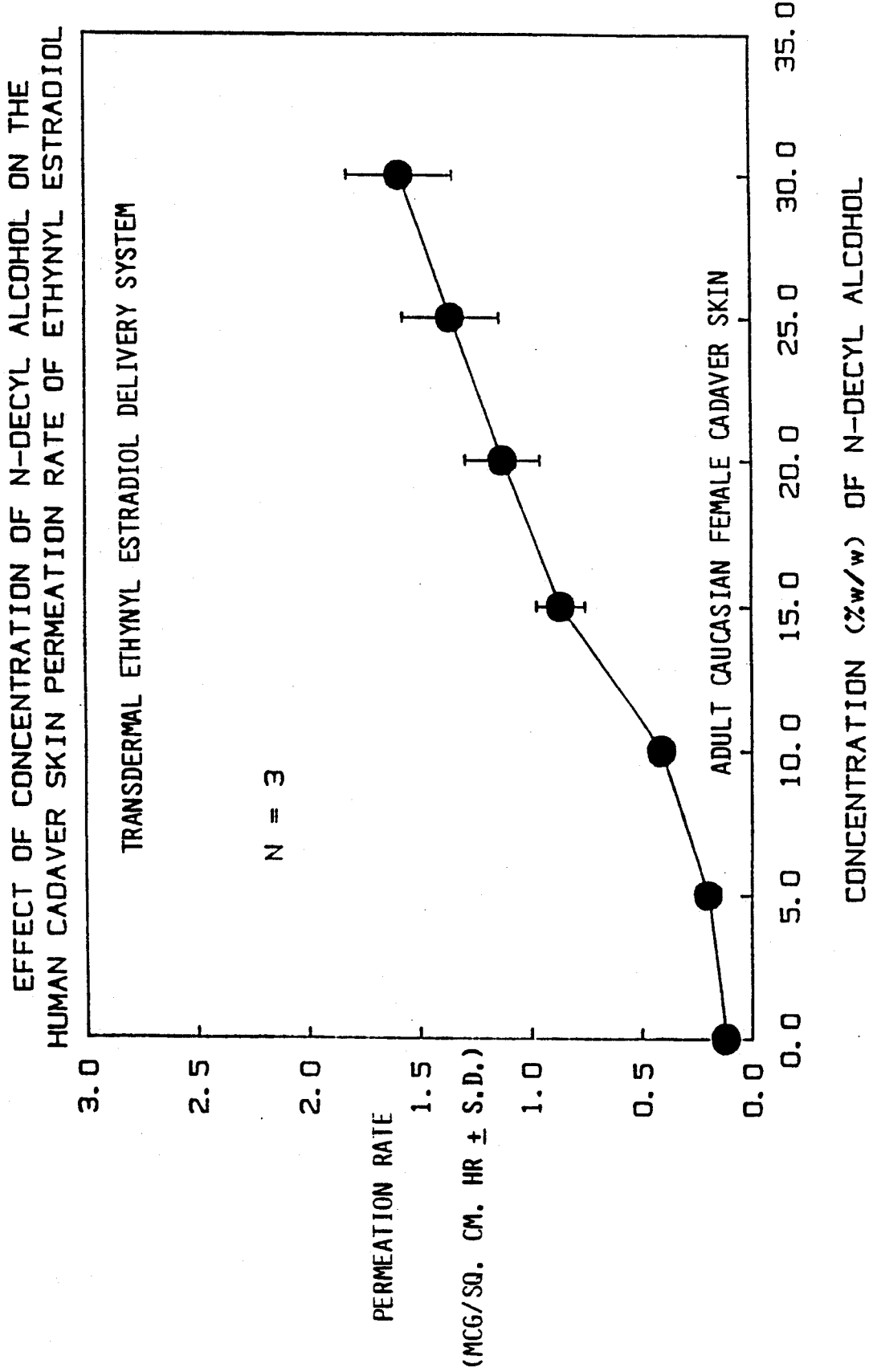
FIG. 9 is a graph showing the effect of concentration of n-decyl alcohol in a dosage unit on the human cadaver skin permeation rate of ethinyl estradiol.
Figure 10:
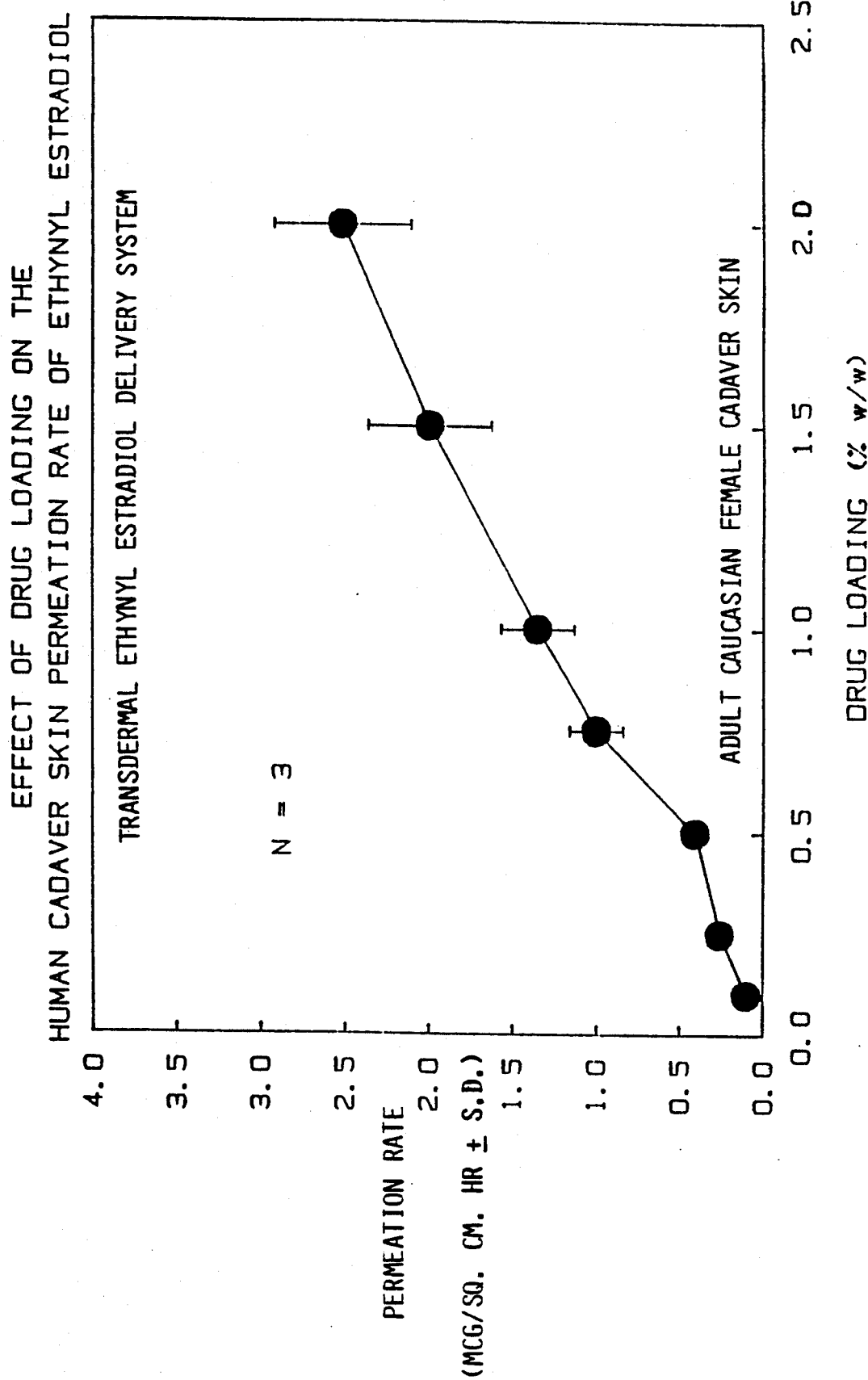
FIG. 10 is a graph showing the effect of drug loading in a dosage unit on the human cadaver skin permeation rate of ethinyl estradiol.
Figure 11:
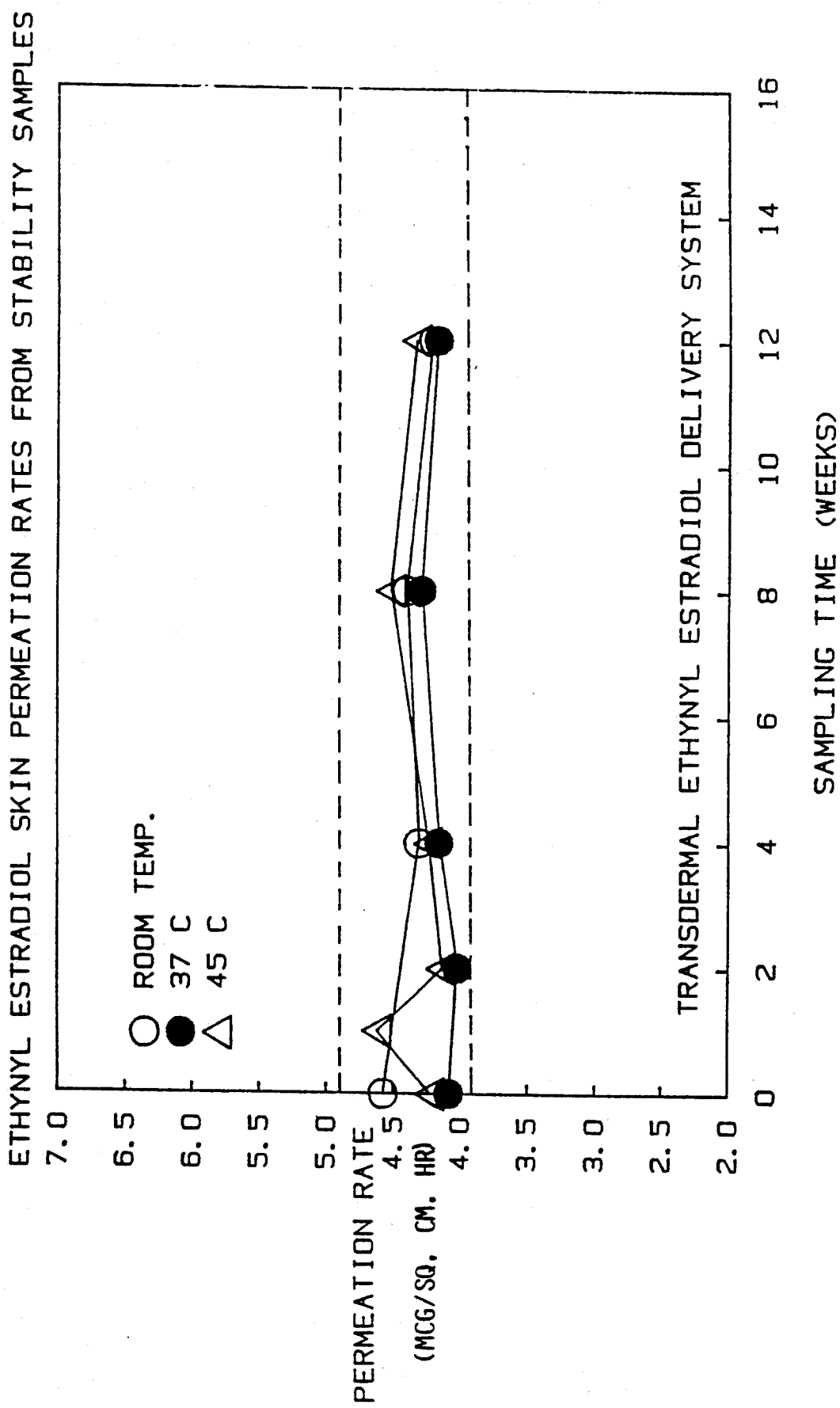
FIG. 11 is a graph of ethinyl estradiol skin permeation rates from dosage unit stability samples.
Figure 12:
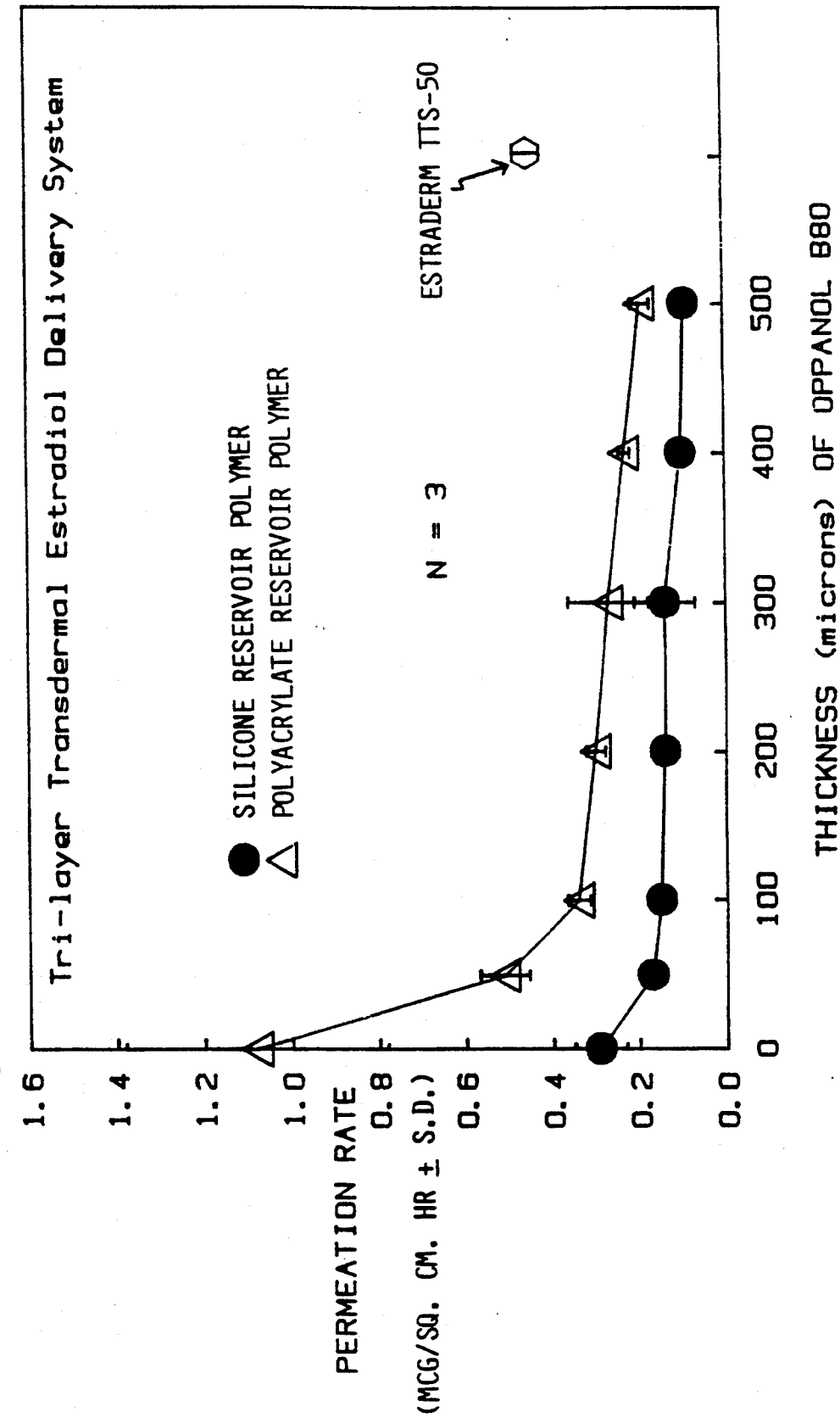
FIG. 12 is a graph showing, in a dosage unit, the effect of thickness of an adhesive polymer layer separating the adhesive polymer drug reservoir layer and an enhancer-containing adhesive polymer layer designed for contact with skin of subject.
Figure 13:
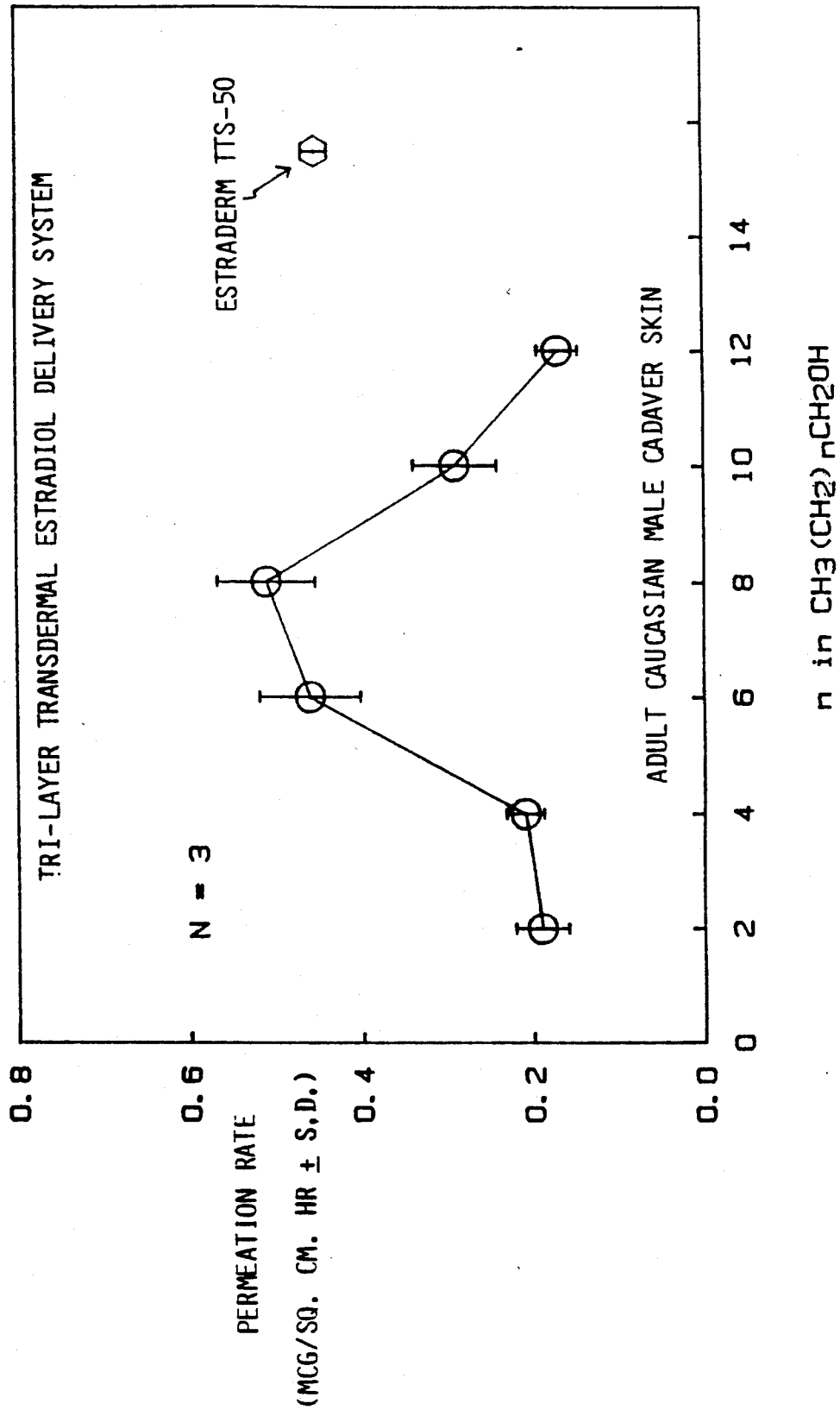
FIG. 13 is a graph showing the effect of the chain length of alkanols as enhancer in a dosage unit on the human cadaver skin permeation rate of estradiol.
Figure 14:
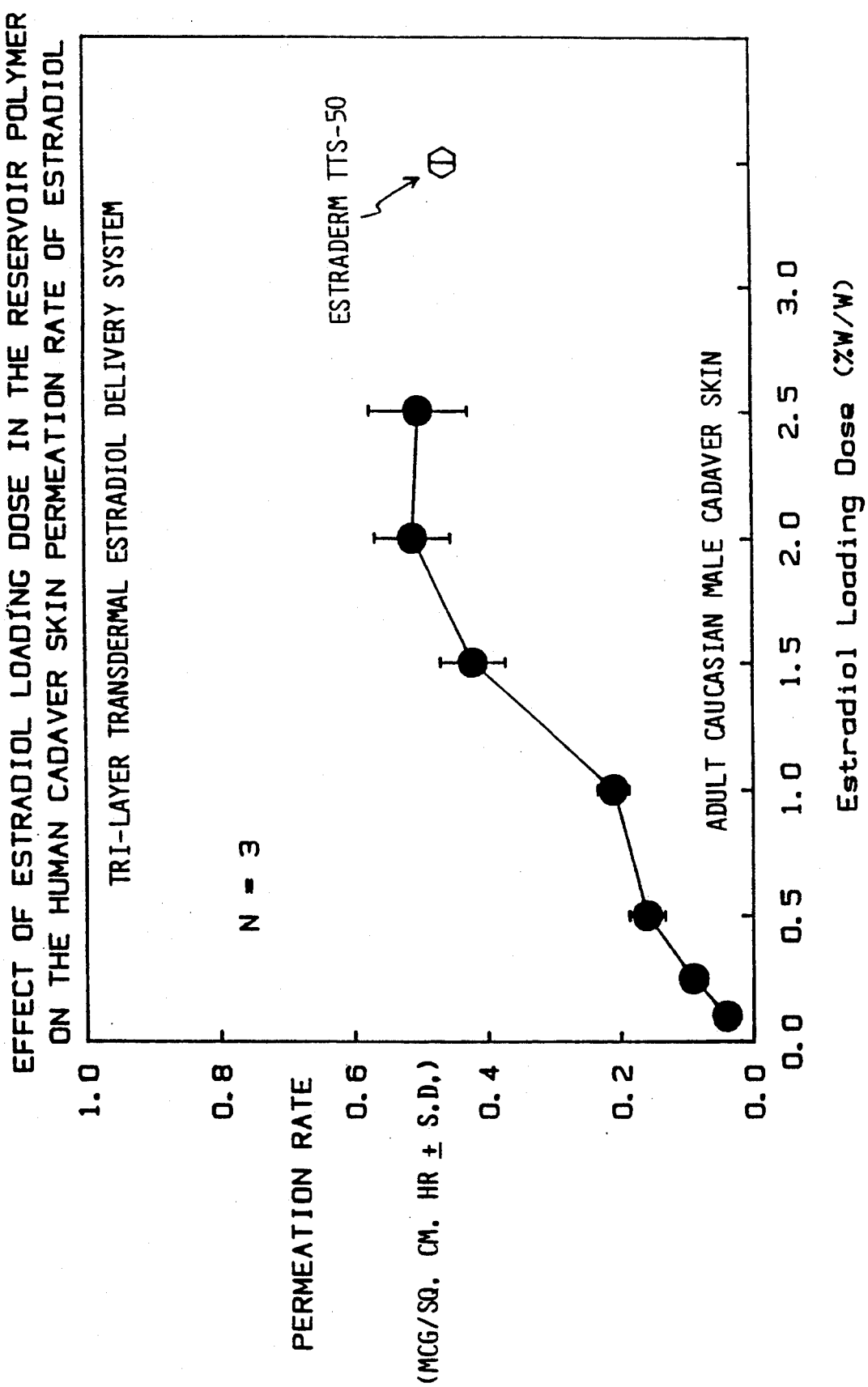
FIG. 14 is a graph showing the effect of estradiol loading dose in the reservoir adhesive polymer layer of a dosage unit on the human cadaver skin permeation rate of estradiol.
Figure 15:
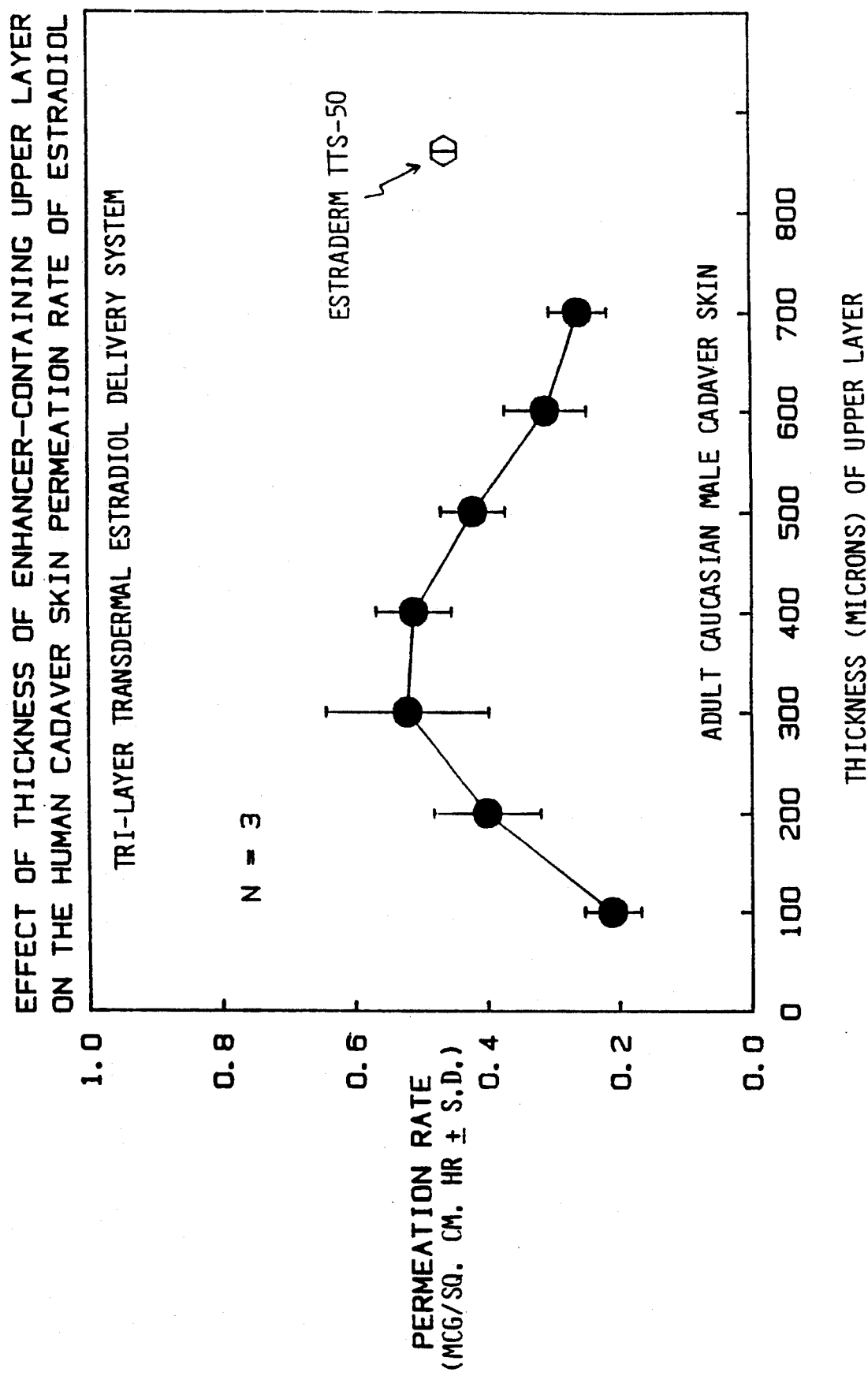
FIG. 15 is a graph showing the effect of the thickness of enhancer-contanining upper layer in a dosage unit on the human cadaver skin permeation rate of estradiol.
Figure 16:
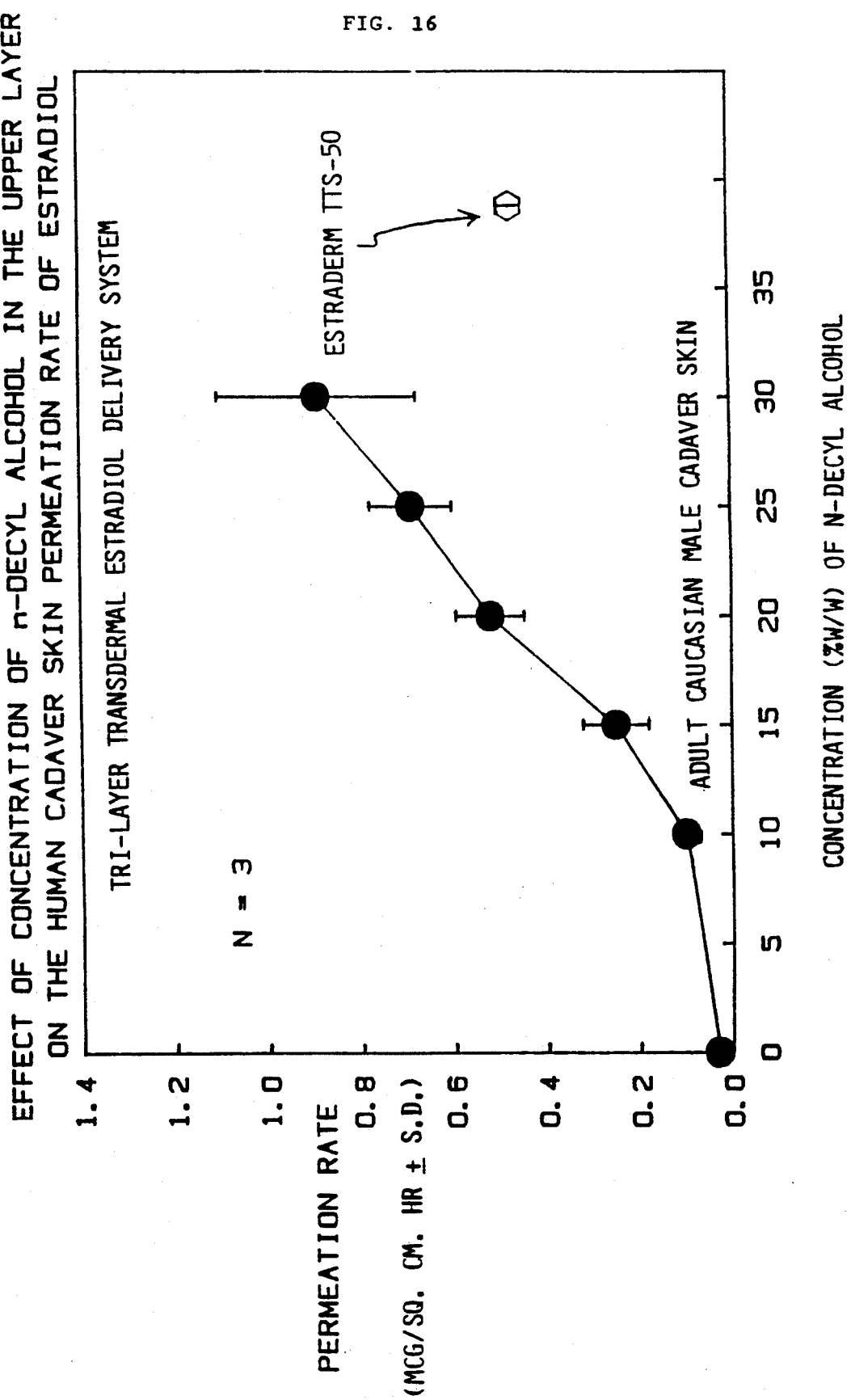
FIG. 16 is a graph showing the effect of concentration of n-decyl alcohol in the upper layer of a dosage unit on the human cadaver skin permeation rate of estradiol.
Figure 17:
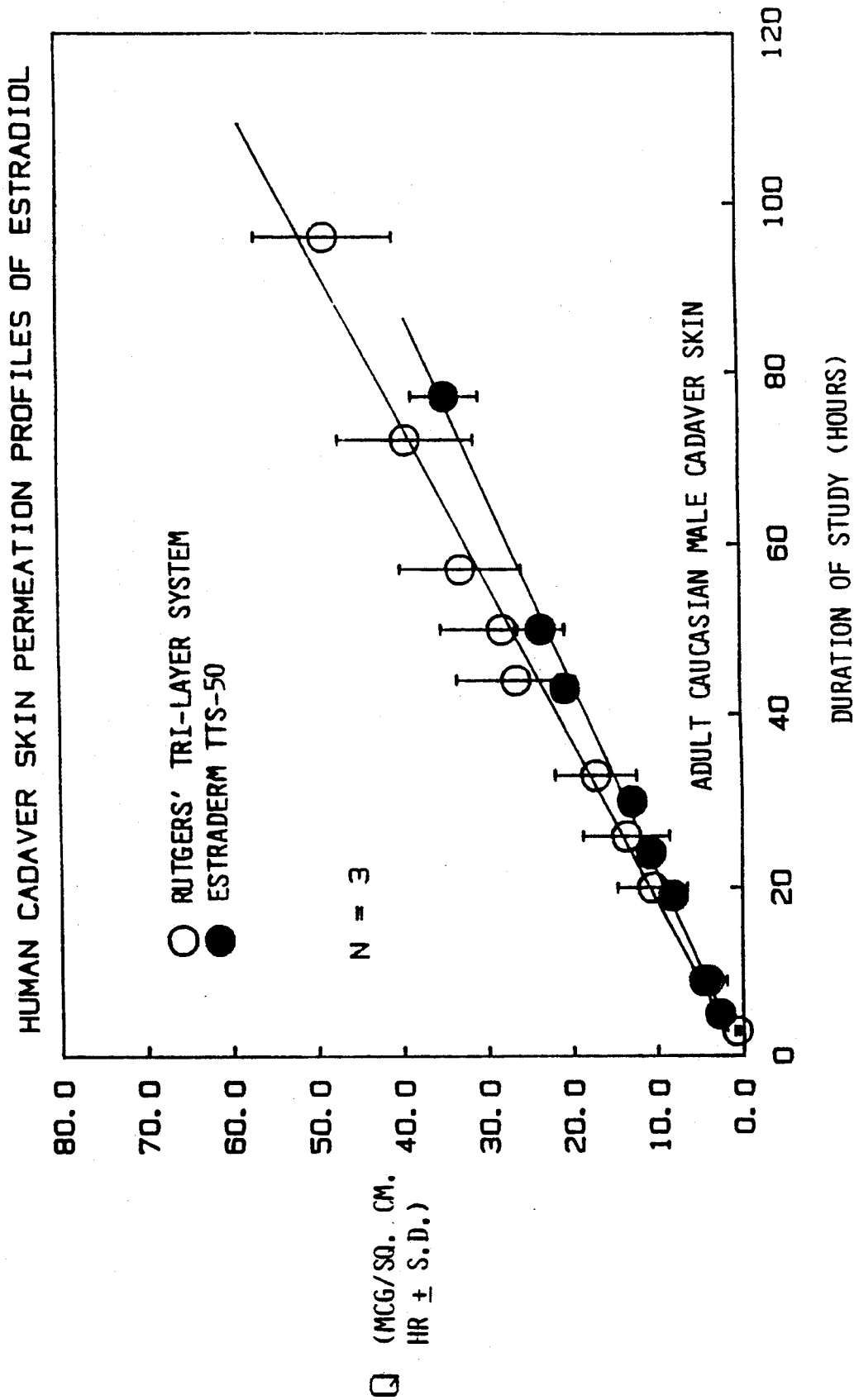
FIG. 17 is a graph comparing human cadaver skin permeation profiles of estradiol from a Rutgers tri-layer dosage unit as compared to Estraderm.
Figure 18:
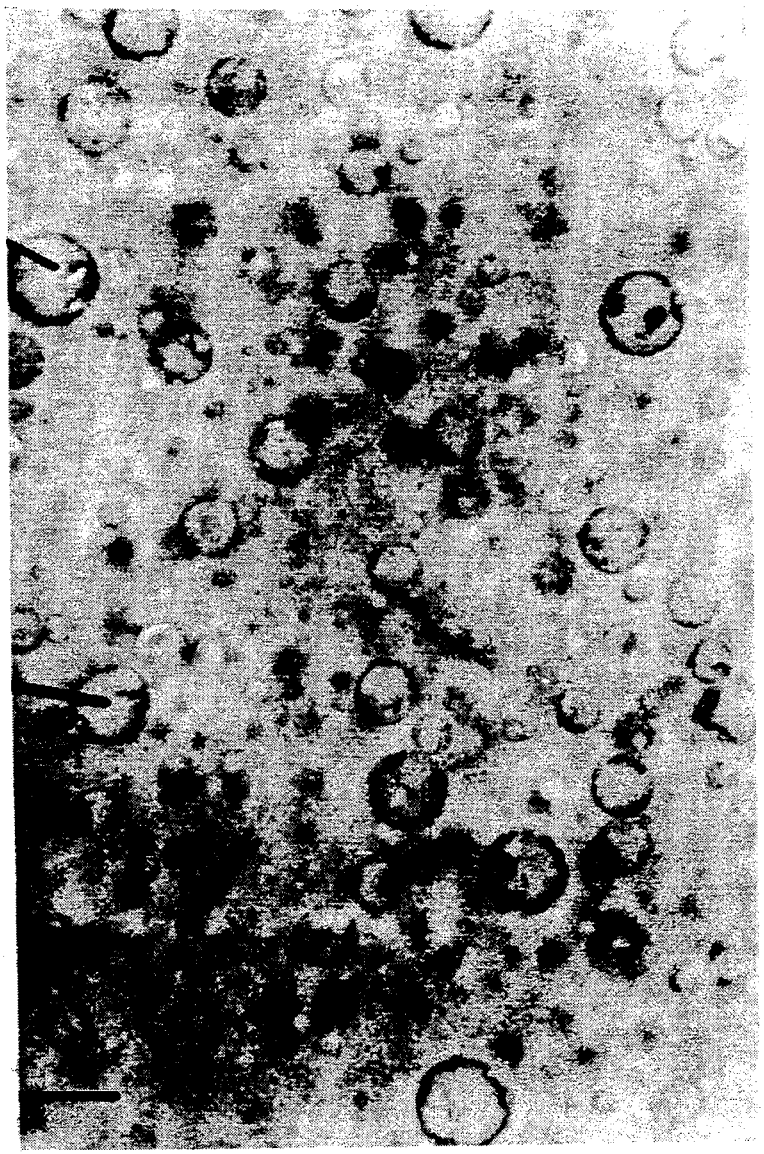
FIG. 18 is a photomicrograph at 635× magnification of a section of an adhesive polymer drug reservoir layer showing transdermal absorption enhancer microreservoirs containing drug (estradiol).

Dosage units of the tri-layer transdermal estradiol delivery system thus prepared were evaluated in vitro using the commercially available product Estraderm TTS-50 (Ciba Geigy) as control. As shown in FIG. 7, the Rutgers' trilayer transdermal estradiol delivery system give slightly higher human cadaver skin permeation rate of estradiol than the Estraderm TTS-50 (0.51±0.057 vs 0.45±0.021 mcg/sq. cm/hr, N=3). This steady state permeation rate of estradiol delivered from Rutgers' system was found to last for as long as 140 hours which allows this system to be used as once-a-week transdermal estradiol delivery system.

What is claimed is:

1. A transdermal dosage unit for treatment of postmenopausal syndrome having the following backing layer and adhesive polymer layer:
   a) a backing layer which is substantially impervious to an effective estrogen to be delivered transdermally from the adhesive polymer layer and transdermal absorption agent components of the adhesive polymer layer; and
   b) an adhesive polymer layer which is adhered to said backing layer and which has dispersed therein within microreservoirs an effective daily dosage amount of an estrogen effective in treatment of postmenopausal syndrome, said adhesive polymer being biocompatible, compatible with said estrogen and permitting said estrogen to be transdermally absorbed; said adhesive polymer layer having one or more transdermal absorption enhancing agents microdispersed therein predominantly on a weight basis in the form of microreservoirs having diameters within the range of about 1 to about 150 microns, said transdermal absorption agent or agents selected from biocompatible compounds having at least six carbon atoms and which are capable of forming microreservoirs during microdispersion with said adhesive polymer and estrogen to encapsulate said estrogen in said adhesive polymer used to encapsulate said estrogen in said adhesive polymer used to make said adhesive polymer layer and being substantially insoluble or insoluble in water; said dosage unit capable of delivering to the subject being treated a daily estrogen dosage for at least a term of one day to about seven successive days.

2. A transdermal dosage unit of claim 1 in which the estrogen is selected from ethinyl estradiol, 17-beta-estradiol, bioconvertible derivatives thereof, and combinations thereof.

3. A transdermal dosage unit of claim 1 which has an effective amount of a compound selected from the group consisting of progestogens and progestins, which are capable of transdermal absorption, and combinations thereof.

4. A transdermal dosage unit of claim 1 which has an effective amount of 17-beta-estradiol as said estrogen and an effective amount of progesterone present in said adhesive polymer microreservoir layer.

5. A transdermal dosage unit of claim 1 in which the transdermal absorption enhancing agent used to provide said microreservoirs is n-decyl alcohol.

6. A transdermal dosage unit of claim 1 in which the diameters of the microreservoirs are within the range of about 2 to about 100 microns.

7. A transdermal dosage unit for treatment of postmenopausal syndrome having the following backing layer and adhesive polymer layer:
   a) A backing layer which is substantially impervious to an effective estrogen to be delivered transdermally from the adhesive polymer layer and transdermal absorption agent components of the adhesive polymer layer; and
   b) An adhesive polymer layer which is adhered to said backing layer and which has microdispersed therein an effective daily dosage amount of an estrogen effective in treatment of postmenopausal syndrome, said adhesive polymer being biocompatible, compatible with said estrogen and permitting said estrogen to be transdermally absorbed;
said dosage unit capable of delivering to the subject being treated a daily estrogen dosage for at least a term of one day to about seven successive days.

8. A transdermal dosage unit of claim 7 in which the estrogen is selected from ethinyl estradiol, 17-beta-estradiol, bioconvertible derivatives thereof, and combinations thereof.

9. A transdermal dosage unit of claim 7 which has an effective amount of a compound selected from the group consisting of progesterone and progestins, which are capable of transdermal absorption, and combinations thereof.

10. A transdermal dosage unit of claim 7 which has an effective amount of 17-beta-estradiol as said estrogen and an effective amount of progesterone.

11. A transdermal dosage unit of claim 7 which has an additional adhesive polymer layer in intimate contact with said adhesive polymer layer containing estrogen which is made from an adhesive polymer which is substantially free of estrogen.

12. A transdermal dosage unit of claim 11 in which an effective amount of a transdermal absorption enhancing agent is dispersed in the additional adhesive-polymer layer.

13. A transdermal dosage unit of claim 12 wherein the transdermal absorption enhancing agent is n-decyl alcohol.

14. A transdermal dosage unit of claim 11 wherein said adhesive polymer layer having present estrogen and said additional adhesive polymer layer are separated by, but are in respective intimate contact therewith, a biocompatible adhesive polymer separating layer through which said estrogen is transmitted for desired transdermal absorption, said separating layer made using an adhesive polymer which is free or substantially free of estrogen, progestin and enhancing agents.

15. A transdermal dosage unit of claim 14 which has ethinyl estradiol or 17-beta-estradiol or combinations thereof as said estrogen component.

16. A transdermal dosage unit of claim 14 wherein the separating layer is made from a bioacceptable adhesive polymer having a sufficiently high viscosity or molecular weight to provide a dimensionally stable separating layer and a substantial reduction in the transmission rate of said estrogen component.

17. A transdermal dosage unit of claim 14 wherein the dosage unit has an effective amount of a member of the group consisting of bioacceptable progestogens and progestins, and bioconvertible derivatives thereof, which are capable of transdermal absorption.

18. A transdermal dosage unit of claim 16 where the separating layer is made from a polyisobutylene adhesive.

19. A process for using dosage units as defined in claim 1 for treating postmenopausal syndrome by applying to the skin of a subject desiring said treatment said dosage units successively to provide effective daily dosage amounts of said estrogen for as long as said treatment is desired.

20. A process for using dosage units as defined in claim 7 for treating postmenopausal syndrome by applying to the skin of a subject desiring said treatment said dosage units successively to provide effective daily dosage amount of said estrogen for as long as said treatment is desired.

* * * * *